United States Patent
Bonini et al.

(10) Patent No.: US 10,155,011 B2
(45) Date of Patent: Dec. 18, 2018

(54) TARGETED DISRUPTION OF T CELL RECEPTOR GENES USING ENGINEERED ZINC FINGER PROTEIN NUCLEASES

(71) Applicants: Sangamo BioSciences, Inc., Richmond, CA (US); Ospedale San Raffaele srl, Milan (IT)

(72) Inventors: Maria Chiara Bonini, Milan (IT); Pietro Genovese, Milan (IT); Philip D. Gregory, Richmond, CA (US); Michael C. Holmes, Richmond, CA (US); Luigi Naldini, Milan (IT); David Paschon, Richmond, CA (US); Elena Provasi, Milan (IT); Lei Zhang, Richmond, CA (US)

(73) Assignees: Sangamo Therapeutics, Inc., Richmond, CA (US); Ospedale San Raffaele srl, Milan (IT)

( * ) Notice: Subject to any disclaimer, the term of this patent is extended or adjusted under 35 U.S.C. 154(b) by 183 days.

(21) Appl. No.: 14/591,625

(22) Filed: Jan. 7, 2015

(65) Prior Publication Data
US 2015/0164954 A1 Jun. 18, 2015

Related U.S. Application Data

(63) Continuation of application No. 12/927,292, filed on Nov. 10, 2010, now Pat. No. 8,956,828.

(60) Provisional application No. 61/280,863, filed on Nov. 10, 2009, provisional application No. 61/404,064, filed on Sep. 27, 2010, provisional application No. 61/404,685, filed on Oct. 6, 2010.

(51) Int. Cl.
| | | |
|---|---|---|
| *C12N 15/85* | (2006.01) | |
| *A61K 35/28* | (2015.01) | |
| *C12N 9/22* | (2006.01) | |
| *A61K 35/17* | (2015.01) | |
| *C07K 14/725* | (2006.01) | |
| *C12N 15/01* | (2006.01) | |
| *A61K 35/00* | (2006.01) | |
| *A61K 38/00* | (2006.01) | |

(52) U.S. Cl.
CPC ............ *A61K 35/28* (2013.01); *A61K 35/17* (2013.01); *C07K 14/7051* (2013.01); *C12N 9/22* (2013.01); *C12N 15/01* (2013.01); *A61K 35/00* (2013.01); *A61K 38/00* (2013.01); *C07K 2319/81* (2013.01); *C07K 2319/95* (2013.01)

(58) Field of Classification Search
CPC ........ A61K 35/28; A61K 35/17; A61K 35/00; A61K 38/00; C07K 14/7051; C07K 2319/81; C07K 2319/95; C12N 15/01; C12N 9/22
See application file for complete search history.

(56) References Cited

U.S. PATENT DOCUMENTS

| | | | |
|---|---|---|---|
| 5,198,338 A | * | 3/1993 | Croce .................. C12Q 1/6886 435/6.14 |
| 5,356,802 A | | 10/1994 | Chandrasegaran |
| 5,436,150 A | | 7/1995 | Chandrasegaran |
| 5,487,994 A | | 1/1996 | Chandrasegaran |
| 5,789,538 A | | 8/1998 | Rebar et al. |
| 5,925,523 A | | 7/1999 | Dove et al. |
| 6,007,988 A | | 12/1999 | Choo et al. |
| 6,013,453 A | | 1/2000 | Choo et al. |
| 6,140,081 A | | 10/2000 | Barbas |
| 6,140,466 A | | 10/2000 | Barbas et al. |
| 6,200,759 B1 | | 3/2001 | Dove et al. |
| 6,242,568 B1 | | 6/2001 | Barbas et al. |
| 6,410,248 B1 | | 6/2002 | Greisman et al. |
| 6,453,242 B1 | | 9/2002 | Eisenberg et al. |
| 6,503,717 B2 | | 1/2003 | Case et al. |
| 6,534,261 B1 | | 3/2003 | Cox et al. |
| 6,599,692 B1 | | 7/2003 | Case et al. |

(Continued)

FOREIGN PATENT DOCUMENTS

| | | |
|---|---|---|
| EP | 1956080 | 8/2008 |
| GB | 2338237 A | 12/1999 |

(Continued)

OTHER PUBLICATIONS

Porteus. "Mammalian Gene Targeting with Designed Zinc Finger Nucleases." Molecular Therapy (2006) 13, 438-446.*
Takahashi et al. "Clonal Expansion of CD4+ TCRββ+ T Cells in TCR α-Chain-Deficient Mice by Gut-Derived Antigens." The Journal of Immunology Feb. 1, 1999 vol. 162 No. 3 pp. 1843-1850.*
Boch et al. "Breaking the code of DNA binding specificity of TAL-type III effectors." Science. Dec. 11, 2009;326(5959)1509-12.*

(Continued)

*Primary Examiner* — Titilayo Moloye
(74) *Attorney, Agent, or Firm* — Dahna S. Pasternak; Pasternak Patent Law

(57) ABSTRACT

Disclosed herein are methods and compositions for inactivating TCR genes, using zinc finger nucleases (ZFNs) comprising a zinc finger protein and a cleavage domain or cleavage half-domain in conditions able to preserve cell viability. Polynucleotides encoding ZFNs, vectors comprising polynucleotides encoding ZFNs and cells comprising polynucleotides encoding ZFNs and/or cells comprising ZFNs are also provided. Disclosed herein are also methods and compositions for expressing a functional exogenous TCR in the absence of endogenous TCR expression in T lymphocytes, including lymphocytes with a central memory phenotype. Polynucleotides encoding exogenous TCR, vectors comprising polynucleotides encoding exogenous TCR and cells comprising polynucleotides encoding exogenous TCR and/or cells comprising exogenous TCR are also provided.

13 Claims, 21 Drawing Sheets

Specification includes a Sequence Listing.

(56) References Cited

U.S. PATENT DOCUMENTS

| | | | |
|---|---|---|---|
| 6,607,882 B1 | 8/2003 | Cox et al. | |
| 6,689,558 B2 | 2/2004 | Case | |
| 6,824,978 B1 | 11/2004 | Cox et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,163,824 B2 | 1/2007 | Cox et al. | |
| 8,921,332 B2 | 12/2014 | Choulika et al. | |
| 9,181,527 B2 | 11/2015 | Sentman | |
| 2003/0232410 A1 | 12/2003 | Liljedahl et al. | |
| 2005/0026157 A1 | 2/2005 | Baltimore et al. | |
| 2005/0064474 A1 | 3/2005 | Umov et al. | |
| 2005/0208489 A1 | 9/2005 | Carroll et al. | |
| 2006/0188987 A1 | 8/2006 | Guschan et al. | |
| 2006/0200869 A1 | 9/2006 | Naldini et al. | |
| 2007/0116690 A1* | 5/2007 | Yang | A01K 67/0271 424/93.21 |
| 2007/0134796 A1 | 6/2007 | Holmes et al. | |
| 2007/0213269 A1 | 9/2007 | Barbas et al. | |
| 2007/0218528 A1 | 9/2007 | Miller et al. | |
| 2008/0015164 A1 | 1/2008 | Collingwood | |
| 2008/0131962 A1 | 6/2008 | Miller | |
| 2008/0159996 A1* | 7/2008 | Ando | C07K 14/4703 424/93.21 |
| 2008/0299580 A1 | 12/2008 | DeKelver et al. | |
| 2009/0117617 A1 | 5/2009 | Holmes et al. | |
| 2010/0273213 A1* | 10/2010 | Mineno | C07K 14/7051 435/69.1 |
| 2011/0129898 A1 | 6/2011 | Doyon | |
| 2011/0201058 A1 | 8/2011 | Doyon et al. | |
| 2012/0321667 A1 | 12/2012 | Sentman | |

FOREIGN PATENT DOCUMENTS

| | | | | |
|---|---|---|---|---|
| WO | WO 95/19431 A1 | 7/1995 | | |
| WO | WO 96/06166 A1 | 2/1996 | | |
| WO | WO 98/37186 A1 | 8/1998 | | |
| WO | WO 98/53057 A1 | 11/1998 | | |
| WO | WO 98/53058 A1 | 11/1998 | | |
| WO | WO 98/53059 A1 | 11/1998 | | |
| WO | WO 98/53060 A1 | 11/1998 | | |
| WO | WO 98/54311 A1 | 12/1998 | | |
| WO | WO 00/27878 A1 | 5/2000 | | |
| WO | WO 01/60970 A2 | 8/2001 | | |
| WO | WO 01/88197 A2 | 11/2001 | | |
| WO | WO 02/016536 A1 | 2/2002 | | |
| WO | WO 02/077227 A2 | 10/2002 | | |
| WO | WO 02/099084 A2 | 12/2002 | | |
| WO | WO 03/016496 A2 | 2/2003 | | |
| WO | WO 06/010834 A1 | 2/2006 | | |
| WO | WO 07/014275 A2 | 1/2007 | | |
| WO | WO 07/139898 A2 | 12/2007 | | |
| WO | WO 2010079430 A1 * | 7/2010 | | C07K 14/195 |
| WO | WO 11/059836 A2 | 5/2011 | | |

OTHER PUBLICATIONS

Moscou and Bogdanove. "A simple cipher governs DNA recognition by TAL effectors." A simple cipher governs DNA recognition by TAL effectors.*

Pennisi E. "The tale of the TALEs." Science. Dec. 14, 2012;338(6113)1408-11.*

Baer et al. "Organization of the T-cell receptor alpha-chain gene and rearrangement in human T-cell leukaemias." Mol Biol Med. Jun. 1986;3(3):265-77.*

Pule et al. "A Chimeric T Cell Antigen Receptor that Augments Cytokine Release and Supports Clonal Expansion of Primary Human T Cells." Molecular Therapy (2005) 12, 933-941.*

Cox et al. "Therapeutic genome editing: prospects and challenges." Nat Med. Feb. 2015;21(2):121-31. (Year: 2015).*

Chandrasegaran et al. "Origins of Programmable Nucleases for Genome Engineering." J Mol Biol. Feb. 27, 2016;428(5 Pt B):963-89 (Year: 2016).*

Lee et al. "Designed nucleases for targeted genome editing." Plant Biotechnol J. Feb. 2016;14(2):448-62. (Year: 2016).*

Abdallah et al. "Genome editing for crop improvement: Challenges and opportunities." GM Crops Food. 2015;6(4):183-205 (Year: 2015).*

Abad, et al., "T-Cell Receptor Gene Therapy of Established Tumors in a Murine Melanoma Model," *J. Immunother.* 31:1-6 (2008).

Alvarez, et al. "A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," *Hum. Gene Ther.* 8(5):597-613 (1997).

Amendola, et al., "Coordinate Dual-Gene Transgenesis by Lentiviral Vectors Carrying Synthetic Bidirectional Promoters," *Nature Biotechnology* 23:108-116 (2005).

Beerli, et al., "Engineering Polydactyl Zinc-Finger Transcription Factors," *Nature Biotechnology* 20:135-141 (2002).

Bendle, et al., "Lethal Graft-Versus-Host Disease in Mouse Models of T Cell Receptor Gene Therapy," *Nature Medicine* 16:565-570 (2010).

Bitinate, et al., "Foki Dimerization is Required for DNA Cleavage," *PNAS USA* 95:10570-10575 (1998).

Boon, et al., "Human T Cell Responses Against Melanoma," *Annu Rev Immunol* 24:175-208 (2006).

Burns, et al., "Lack of Specific F-Retroviral Vector Long Terminal Repeat Promoter Silencing in Patients Receiving Genetically Engineered Lymphocytes and Activation Upon Lymphocyte Restimulation," *Blood* 114:2888-2899 (2009).

Choo, et al., "Advances in Zinc Finger Engineering," *Curr. Opin. Struct. Biol.* 10:411-416 (2000).

Dudley, et al., "Cancer Regression and Autoimmunity in Patients After Clonal Repopulation With Antitumor Lymphocytes," *Science* 298:850-854 (2002).

Dudley, et al., "Adoptive Cell Therapy for Patients With Metastatic Melanoma: Evaluation of Intensive Myeloablative Chemoradiation Preparative Regimens," *J. Clin. Oncol.* 26:5233-5299 (2008).

Follenzi, et al., "Generation of HIV-1 Derived Lentiviral Vectors," *Methods Enzymol.* 346:454-465 (2002).

Guo, et al., "Directed Evolution of an Enhanced and Highly Efficient Foki Cleavage Domain for Zinc Finger Nucleases," *J. Mol. Biol.* 400:96-107 (2010).

Holst, et al., "Generation of T-Cell Receptor Retrogenic Mice," *Nature Protoc.* 1:406-417 (2006).

Inoue, et al., "Aberrant Overexpression of the Wilms Tumor Gene (WT1) in Human Leukemia," *Blood* 89:1405-1412 (1997).

Isalan et al., "A Rapid, Generally Applicable Method to Engineer Zinc Fingers Illustrated by Targeting the HIV-1 Promoter," *Nat. Biotechnol.* 19:656-660 (2001).

Kaneko, et al., "IL-7 and IL-15 Allow the Generation of Suicide Gene-Modified Alloreactive Self-Renewing Central Memory Human T Lymphocytes," *Blood* 113:1006-1015 (2009).

Kim, et al., "Chimeric Restriction Endonuclease," *PNAS USA* 91:883-887 (1994).

Kim, et al., "Insertion and Deletion Mutants of Foki Restriction Endonuclease," *J. Biol. Chem.* 269:31978-31981 (1994).

Kuball, et al., "Facilitating Matched Pairing and Expression of TCR Chains Introduced Into Human T Cells," *Blood* 109:2331-2338 (2007).

Leavitt, et al., "Human Immunodeficiency Virus Type 1 Integrase Mutants Retain In Vitro Integrase Activity Yet Fail to Integrate Viral DNA Efficiently During Infection," *J. Virol.* 70(2):721-728 (1996).

Li, et al., "Functional Domains in Fok I Restriction Endonuclease," *PNAS USA* 89:4275-4279 (1992).

Li, et al., "Alteration of the Cleavage Distance of Fok I Restriction Endonuclease by Insertion Mutagenesis," *PNAS USA* 90:2764-2768 (1993).

Lombardo, et al., "Gene Editing in Human Stem Cells Using Zinc Finger Nucleases and Integrase-Defective Lentiviral Vector Delivery," *Nature Biotechnology* 25:1298-1306 (2007).

Morgan, et al., "Cancer Regression in Patients After Transfer of Genetically Engineered Lymphocytes," *Science* 314:126-129 (2006).

(56) References Cited

OTHER PUBLICATIONS

Ni, et al., "Evaluation of Biodistribution and Safety of Adenovirus Vectors Containing Group B Fibers After Intravenous Injection Into Baboons," *Hum. Gene Ther.* 16:664-677 (2005).
Nilsson, et al., "Functionally Distinct Subpopulations of Cord Blood CD34+ Cells are Transduced by Adenoviral Vectors With Serotype 5 or 35 Tropism," *Mol. Ther.* 9:377-388 (2004).
Nilsson, et al., "Development of an Adenoviral Vector System With Adenovirus Serotype 35 Tropism; Efficient Transient Gene Transfer Into Primary Malignant Hematopoietic Cells," *J. Gene Med.* 6:631-641 (2004).
Pabo, et al., "Design and Selection of Novel CYS2-HIS2 Zinc Finger Proteins," *Ann. Rev. Biochem.* 70:313-340 (2001).
Philippe, et al., "Lentiviral Vectors With a Defective Integrase Allow Efficient and Sustained Transgene Expression In Vitro and In Vivo," *Proc. Nat'l. Acad. Sci. USA* 103(47):17684-17689 (2006).
Reddy, et al., "Development of Adenovirus Serotype 35 as a Gene Transfer Vector," *Virology* 311:384-393 (2003).
Roberts, et al., "Rebase: Restriction Enzymes and Methyltransferases," *Nucleic Acids Research* 31:418-420 (2003).
Rosenberg, et al., "Cancer Immunotherapy: Moving Beyond Current Vaccines," *Nat. Med.* 10:909-915 (2004).
Rosenecker, et al., "Adenovirus Infection in Cystic Fibrosis Patients: Implications for the Use of Adenoviral Vectors for Gene Transfer," *Infection* 24:5-8 (1996).
Rubenstein, et al., "Transfer of TCR Genes Into Mature T Cells is Accompanied by the Maintenance of Parental T Cell Avidity," *J. of Immunol.* 170:1209-1217 (2003).
Schroers, et al., "Gene Transfer Into Human T Lymphocytes and Natural Killer Cells by AD5/F35 Chimeric Adenoviral Vectors," *Exp. Hematol.* 32:536-546 (2004).
Segal, et al., "Custom DNA-Binding Proteins Come of Age: Polydactyl Zinc-Finger Proteins," *Curr. Opin. Biotechnol.* 12:632-637 (2001).
Shayakhmetov, et al., "Efficient Gene Transfer Into Human CD34+ Cells by a Retargeted Adenovirus Vector," *J. Virol.* 74:2567-2583 (2000).
Soya, et al., "A Tumor-Targeted and Conditionally Replicating Oncolytic Adenovirus Vector Expressing Trail for Treatment of Liver Metastases," *Mol. Ther.* 9:496-509 (2004).
Sterman, et al., "Adenovirus-Mediated Herpes Simplex Virus Thymidine Kinase/Ganciclovir Gene Therapy in Patients With Localized Malignancy: Results of a Phase I Clinical Trial in Malignant Mesothelioma," *Hum. Gene Ther.* 7:1083-1089 (1998).
Thomas, et al., "Targeting the Wilms Tumor Antigen 1 by TCR Gene Transfer: TCR Variants Improve Tetramer Binding but Not the Function of Gene Modified Human T Cells," *J. of Immunol.* 179:5803-5810 (2007).
Urnov, et al., "Highly Efficient Endogenous Human Gene Correction Using Designed Zinc-Finger Nucleases," *Nature* 435:646-651 (2005).
Van Loenen, et al., "Mixed T Cell Receptor Dimers Harbor Potentially Harmful Neoreactivity," *PNAS USA* 107:10972-10977 (2010).
Welsh, et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," *Hum. Gene Ther.* 2:205-218 (1995).
Imai and Campana, "Genetic Modification of T Cells for Cancer Therapy," Journal of Biological Regulators and Homeostatic Agents 18:62-71 (2004).
Kammertoens and Blankenstein, "Making and Circumventing Tolerance to Cancer," *Eur. J. Immunol.* 39:2345-2353 (2009).
Kondo, et al., "Expression of Recombination-Activating Gene in Mature Peripheral T Cells in Peyer's Patch," *International Immunology* 15(3):393-402 (2003).
Wagner, "Re-Shaping the T Cell Repertoire: TCR Editing and TCR Revision for Good and for Bad," *Clinical Immunology* 123:1-6 (2007).

\* cited by examiner

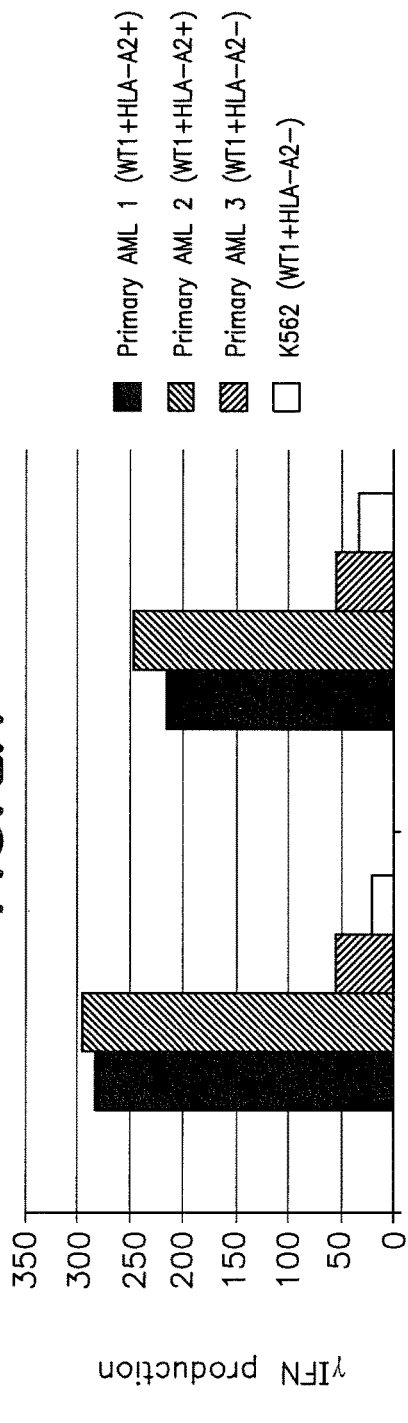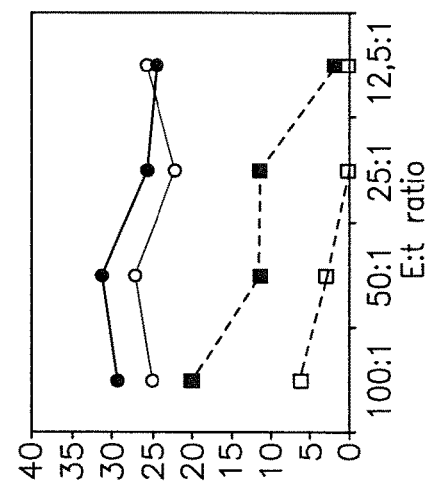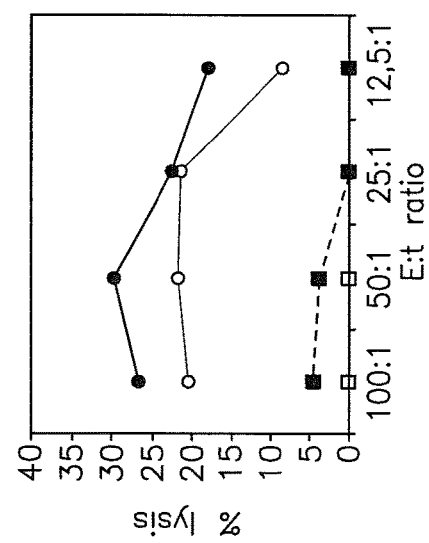

Arrangement of TCRB1 and TBRC2 genes in K562 cells

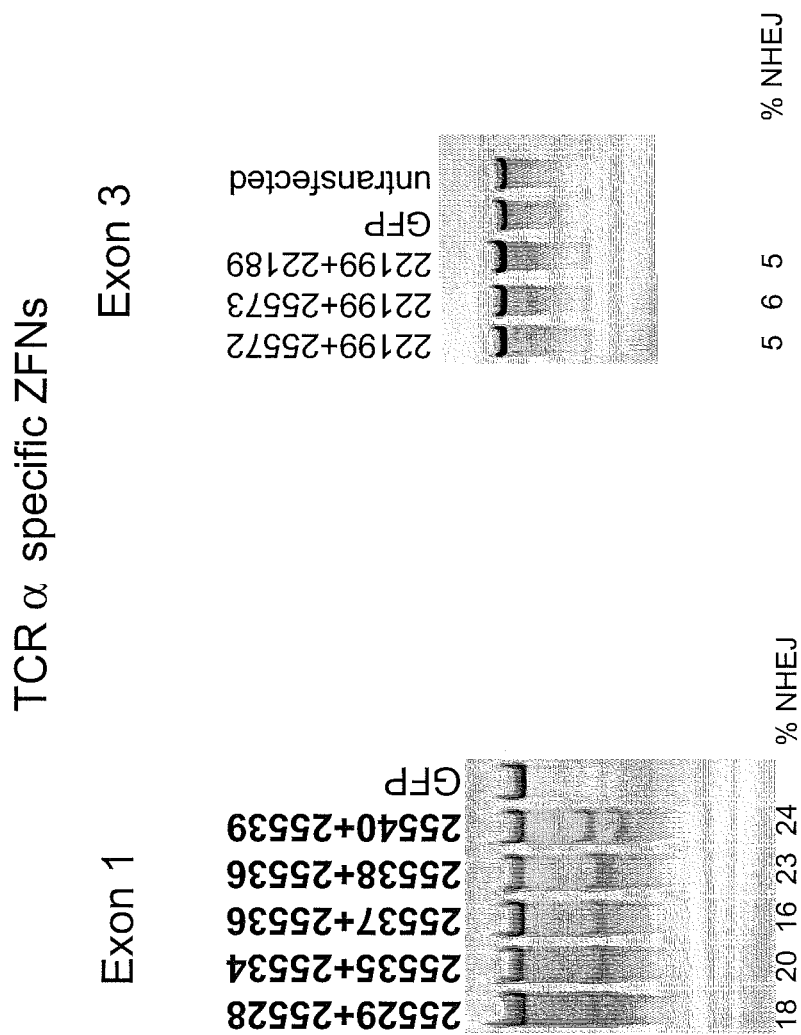

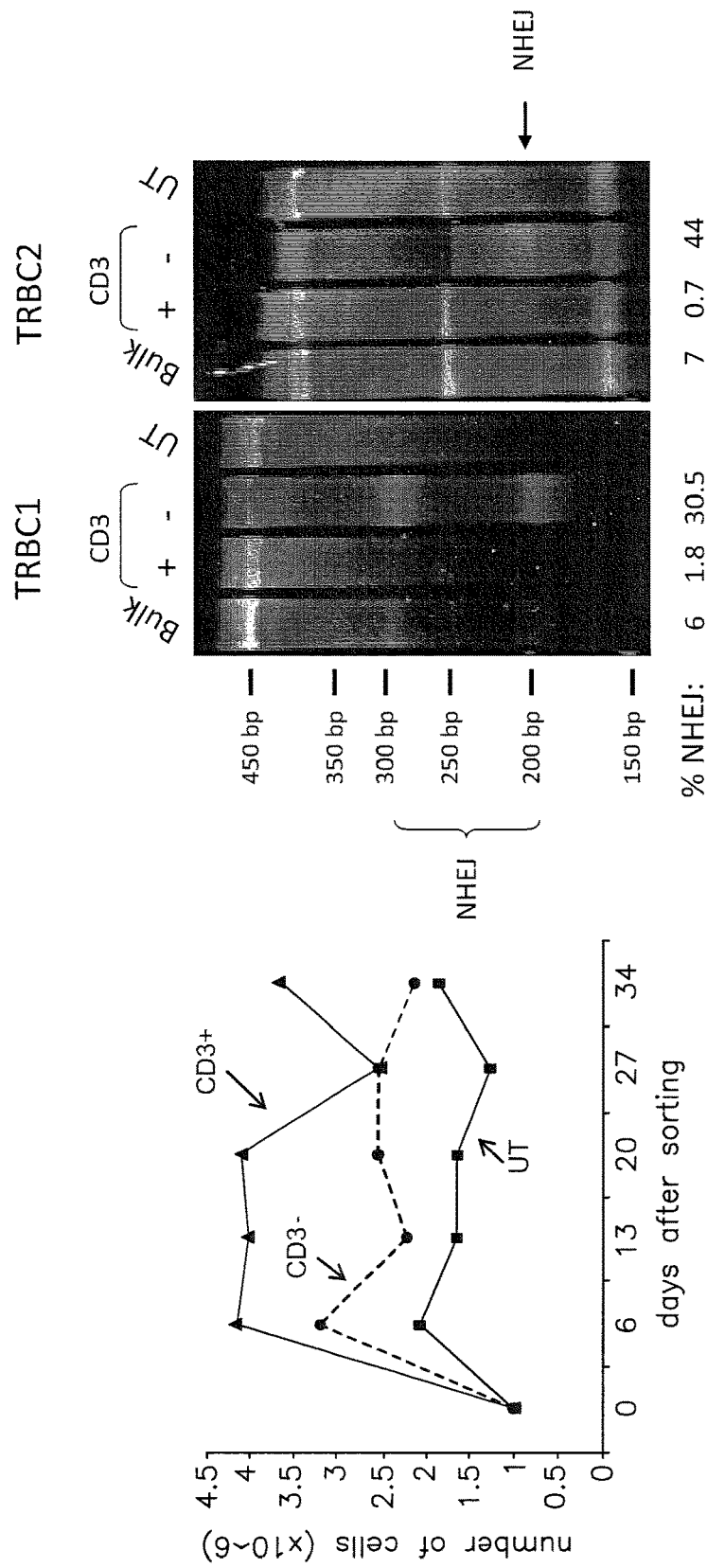

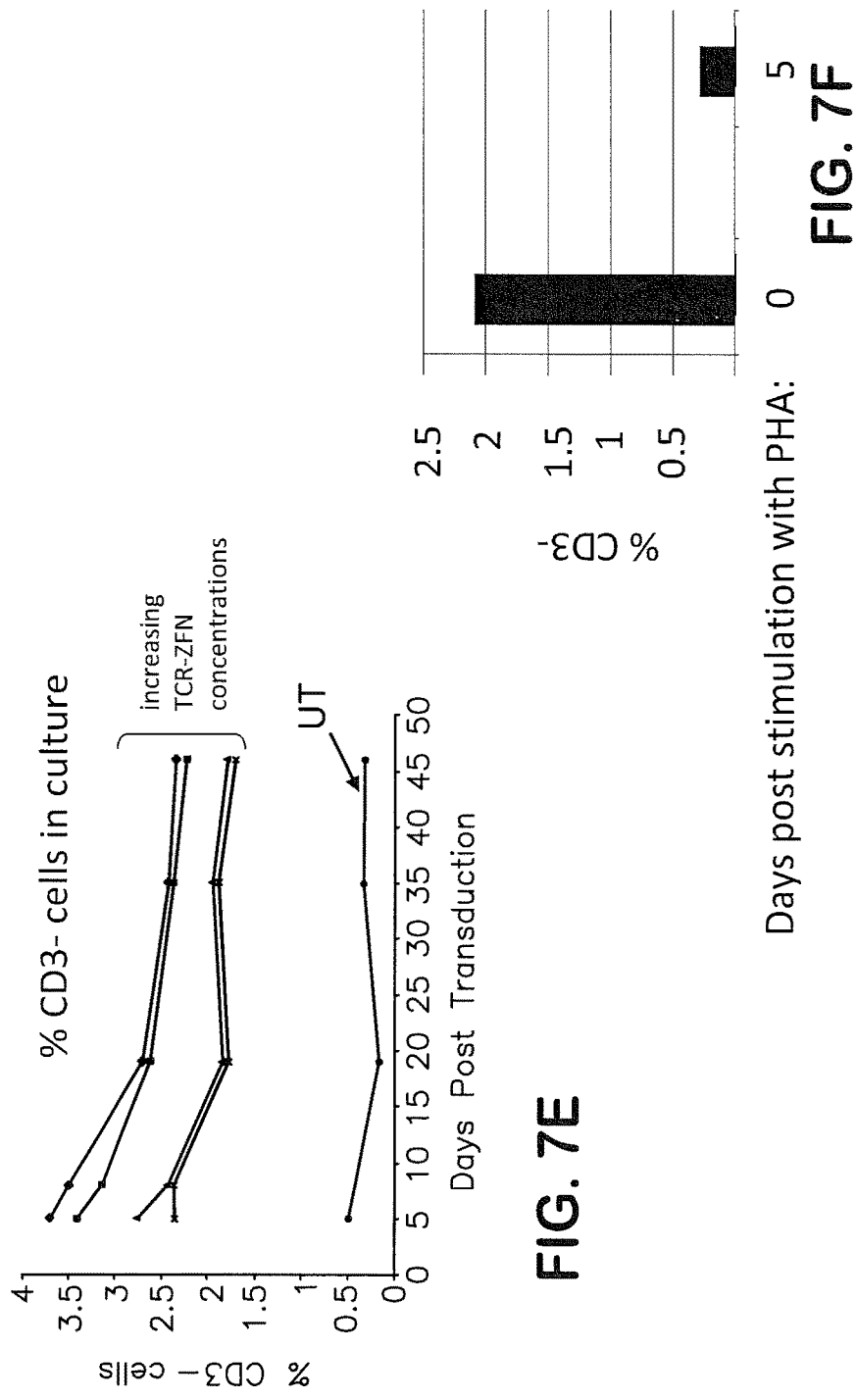

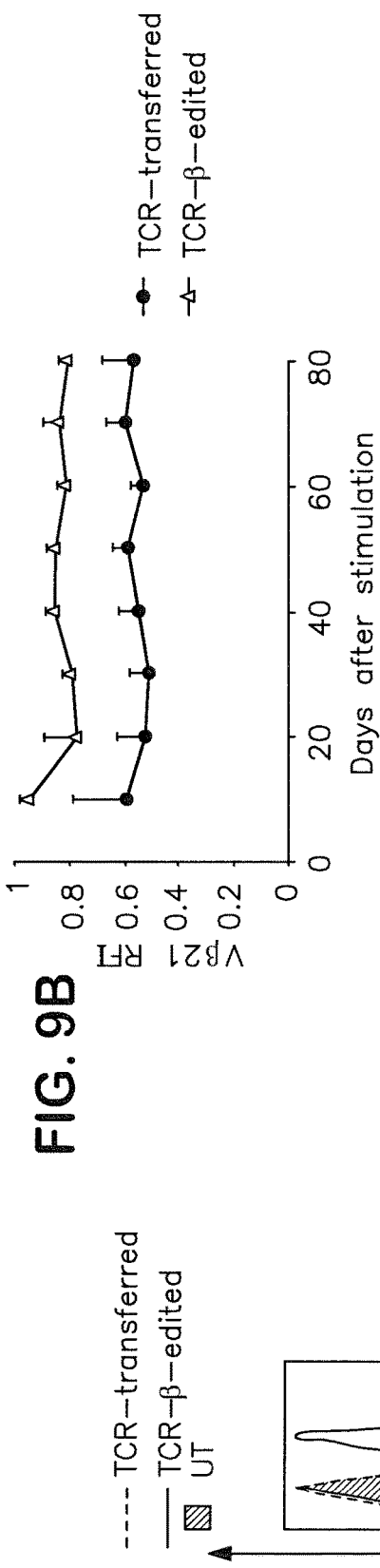
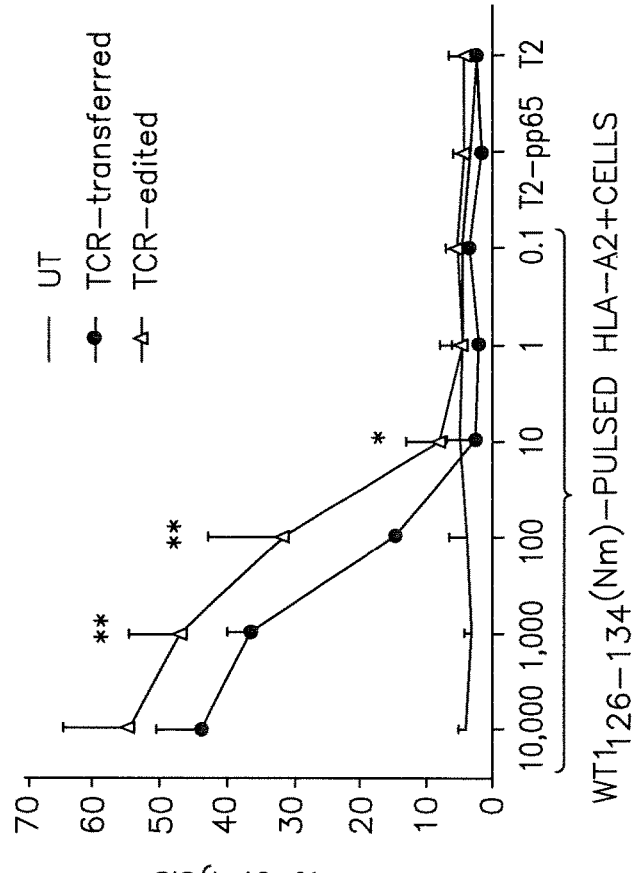
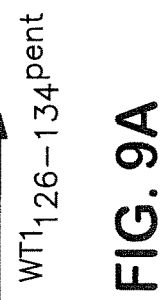
FIG. 9A
FIG. 9B
FIG. 9C

FIG. 13

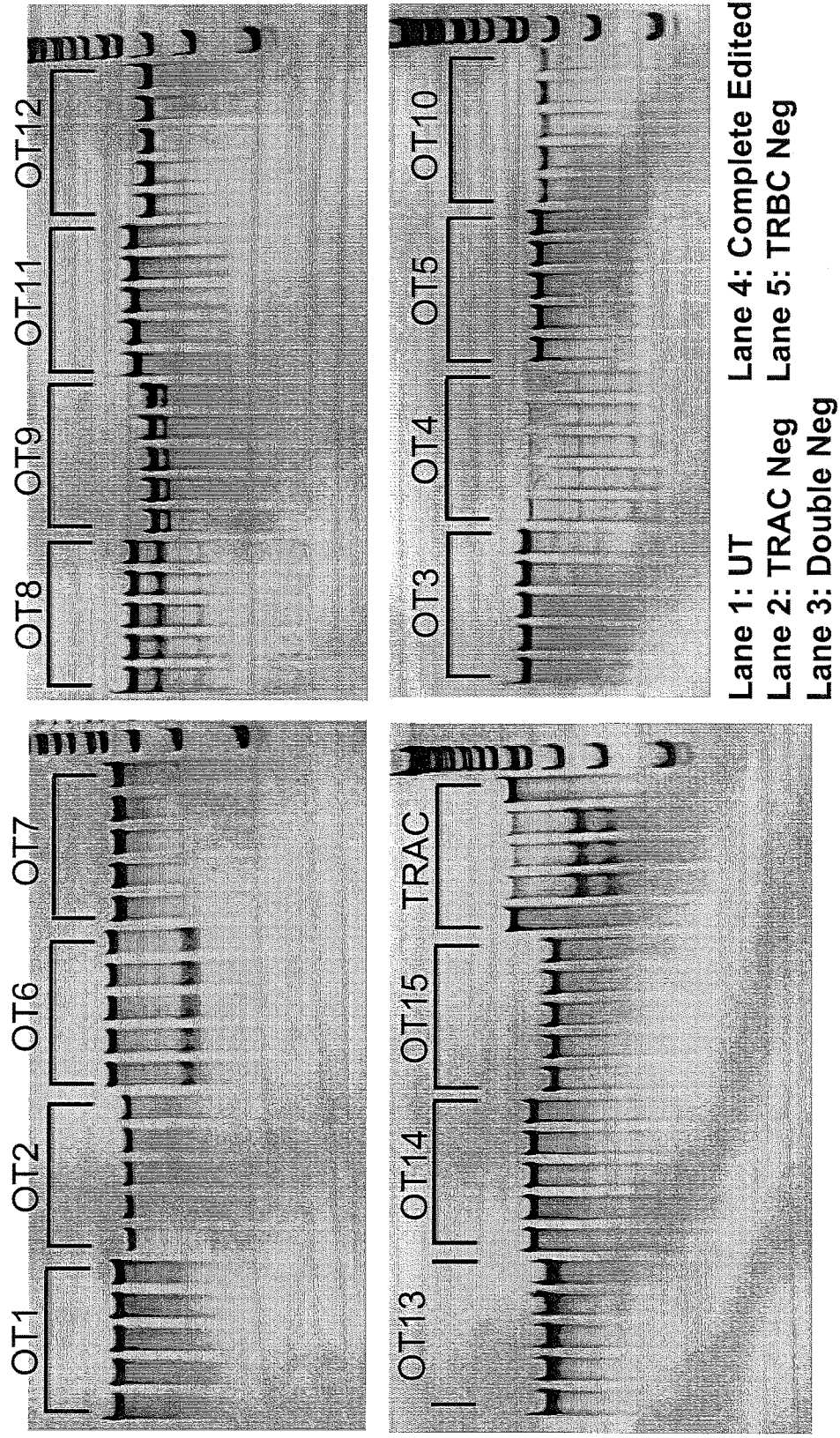

SEQUENCE LISTING

<160> NUMBER OF SEQ ID NOS: 143

<210> SEQ ID NO 1
<211> LENGTH: 28
<212> TYPE: DNA
<213> ORGANISM: Homo sapiens

<400> SEQUENCE: 1
ctatggactt caagagcaac agtgctgt                                          28

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ser Gly Asp Leu Thr Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Arg Thr His Leu Lys Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Gly Asp Arg Asn Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Arg Ser Asn Leu Ser Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Asp Ala Leu Thr Gln
1               5

<210> SEQ ID NO 7
<211> LENGTH: 28
<212> TYPE: DNA
<213> ORGANISM: Homo sapiens

<400> SEQUENCE: 7
ctcatgtcta gcacagtttt gtctgtga                                      28

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ser Gly Ser Leu Ser Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Ser Val Arg Asn Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Asn Leu Ser Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Arg Ser Ala Leu Ala Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Lys Gln Asn Leu Asp Ala
1               5

<210> SEQ ID NO 13
<211> LENGTH: 28
<212> TYPE: DNA
<213> ORGANISM: Homo sapiens

<400> SEQUENCE: 13
gtgctgtggc ctggagcaac aaatctga                                            28

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Arg Ser Ala Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Gly His Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Ser Asp Leu Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Asp Ala Leu Ser Arg
1               5

<210> SEQ ID NO 18
<211> LENGTH: 28
<212> TYPE: DNA
<213> ORGANISM: Homo sapiens

<400> SEQUENCE: 18
ttgctcttga agtccataga cctcatgt                                            28

```
<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Lys Thr Ser Leu Gln Ala
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ser Gly Asn Leu Ala Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Lys Glu Glu Leu Asn Glu
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Ser Asp Leu Ser Arg
1               5

<210> SEQ ID NO 23
<211> LENGTH: 28
<212> TYPE: DNA
<213> ORGANISM: Homo sapiens

<400> SEQUENCE: 23
gctgtggcct ggagcaacaa atctgact                                        28

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Asn Val Asp Leu Ile Glu
```

```
1               5
```

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Arg Ser Ser Asn Leu Ser Arg
1               5
```

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Arg Ser Asp Ala Leu Ser Val
1               5
```

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Asp Ser Ser His Arg Thr Arg
1               5
```

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Trp Arg Ser Cys Arg Ser Ala
1               5
```

<210> SEQ ID NO 29
<211> LENGTH: 28
<212> TYPE: DNA
<213> ORGANISM: Homo sapiens

<400> SEQUENCE: 29

```
ctgttgctct tgaagtccat agacctca                                        28
```

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Ser Ser Asp Arg Lys Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ser Asp Asn Leu Ser Val
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Phe Ile Leu Arg Gly
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Ser Gly Ser Leu Thr Arg
1               5

<210> SEQ ID NO 34
<211> LENGTH: 28
<212> TYPE: DNA
<213> ORGANISM: Homo sapiens

<400> SEQUENCE: 34
ctgtggcctg gagcaacaaa tctgactt                                          28

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Thr Ser Thr Leu Ser Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Asp Ala Leu Ala Arg
1               5

<210> SEQ ID NO 37
<211> LENGTH: 28
<212> TYPE: DNA
<213> ORGANISM: Homo sapiens

<400> SEQUENCE: 37
ctgactttgc atgtgcaaac gccttcaa                                     28

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Arg Ser Ser Leu Ala Ser
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

His Lys Trp Val Leu Arg Gln
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Arg Ser Asn Leu Thr Arg
1               5

<210> SEQ ID NO 41
<211> LENGTH: 28
<212> TYPE: DNA
<213> ORGANISM: Homo sapiens

<400> SEQUENCE: 41
ttgttgctcc aggccacagc actgttgc                                     28

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Trp Gly Thr Arg Tyr Arg
1               5

```
<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Arg Gly Thr Leu Ala Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Asp Asn Leu Arg Glu
1               5

<210> SEQ ID NO 45
<211> LENGTH: 28
<212> TYPE: DNA
<213> ORGANISM: Homo sapiens

<400> SEQUENCE: 45
tgaaagtggc cgggtttaat ctgctcat                                      28

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Ala His Leu Ser Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asp His Leu Ser Val
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Asn Asn His Arg Ile Thr
```

<210> SEQ ID NO 49
<211> LENGTH: 28
<212> TYPE: DNA
<213> ORGANISM: Homo sapiens

<400> SEQUENCE: 49
aggaggattc ggaacccaat cactgaca                                          28

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Arg Ser Asn Leu Val Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Asn Asp Asp Arg Lys Lys
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ser Gly Asn Leu Thr Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ser Ala Asn Leu Ser Arg
1               5

<210> SEQ ID NO 54
<211> LENGTH: 28
<212> TYPE: DNA
<213> ORGANISM: Homo sapiens

<400> SEQUENCE: 54
gaggaggatt cggaacccaa tcactgac                                          28

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Arg Ser Thr Leu Arg Gln
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Ser Gly His Leu Ala Arg
1               5

<210> SEQ ID NO 57
<211> LENGTH: 28
<212> TYPE: DNA
<213> ORGANISM: Homo sapiens

<400> SEQUENCE: 57
tgaaagtggc cgggtttaat ctgctcat                                       28

<210> SEQ ID NO 58
<211> LENGTH: 28
<212> TYPE: DNA
<213> ORGANISM: Homo sapiens

<400> SEQUENCE: 58
ccgtagaact ggacttgaca gcggaagt                                       28

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ser Asp Val Leu Ser Ala
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Arg Ser Asn Arg Ile Lys
1               5

<210> SEQ ID NO 61
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 61

Arg Ser Asp Val Leu Ser Glu
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ser Gly Ser Leu Thr Arg
1               5

<210> SEQ ID NO 63
<211> LENGTH: 28
<212> TYPE: DNA
<213> ORGANISM: Homo sapiens

<400> SEQUENCE: 63
tctcggagaa tgacgagtgg acccagga                                        28

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ser Asp His Leu Ser Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Ser Asp Asn Leu Thr Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Ser Ser Asn Arg Lys Thr
1               5

<210> SEQ ID NO 67
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ser Ala Asn Leu Ala Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Gln Phe Asn Arg Asn Gln
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Ser Ser Asn Leu Ser Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Arg Phe Asn Leu Ser Asn
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu His Phe Gln Leu Thr Gly
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Lys Phe Ala Leu Ala Asn
```

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Gln Ser Gly Ala Leu Ala Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Arg Leu Ser Val Leu Thr Ile
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Asp Arg Ala Asn Leu Thr Arg
1               5

<210> SEQ ID NO 76
<211> LENGTH: 37
<212> TYPE: DNA
<213> ORGANISM: Homo sapiens

<400> SEQUENCE: 76
aggcacaagc aatgtcacaa gtaccatgct tgtactt                          37

<210> SEQ ID NO 77
<211> LENGTH: 37
<212> TYPE: DNA
<213> ORGANISM: Homo sapiens

<400> SEQUENCE: 77
aggtacaagt aaagacgtat gaactttgct tgtactt                          37

<210> SEQ ID NO 78
<211> LENGTH: 37
<212> TYPE: DNA
<213> ORGANISM: Homo sapiens

<400> SEQUENCE: 78
aaatacaagc caagccaagg tggctttgcg tgtaaat                          37

<210> SEQ ID NO 79
<211> LENGTH: 38
<212> TYPE: DNA
<213> ORGANISM: Homo sapiens

```
<400> SEQUENCE: 79
atatacaatt aaagtcagct tttactttgc agttactt                             38

<210> SEQ ID NO 80
<211> LENGTH: 38
<212> TYPE: DNA
<213> ORGANISM: Homo sapiens

<400> SEQUENCE: 80
tagaacatcc aaactctgga ccgactttgc atgtccag                             38

<210> SEQ ID NO 81
<211> LENGTH: 37
<212> TYPE: DNA
<213> ORGANISM: Homo sapiens

<400> SEQUENCE: 81
attcaaacac aaagtcccgt ggattttgct tttaaat                              37

<210> SEQ ID NO 82
<211> LENGTH: 37
<212> TYPE: DNA
<213> ORGANISM: Homo sapiens

<400> SEQUENCE: 82
atgcaggagc aaggtcactc tgaccttcct ttgcctt                              37

<210> SEQ ID NO 83
<211> LENGTH: 37
<212> TYPE: DNA
<213> ORGANISM: Homo sapiens

<400> SEQUENCE: 83
atgcacacac aaactcattt aagctttgct tttccat                              37

<210> SEQ ID NO 84
<211> LENGTH: 37
<212> TYPE: DNA
<213> ORGANISM: Homo sapiens

<400> SEQUENCE: 84
cagcccatgg aatgtcattc tcacattgct tgtgctt                              37

<210> SEQ ID NO 85
<211> LENGTH: 37
<212> TYPE: DNA
<213> ORGANISM: Homo sapiens

<400> SEQUENCE: 85
aagcaaaaga aaaatcaata tgacttggct ttggctt                              37

<210> SEQ ID NO 86
<211> LENGTH: 38
<212> TYPE: DNA
<213> ORGANISM: Homo sapiens

<400> SEQUENCE: 86
aaggtcactc actgtctgtg tggagtttgc gtgtcctc                             38

<210> SEQ ID NO 87
<211> LENGTH: 38
<212> TYPE: DNA
```

<213> ORGANISM: Homo sapiens

<400> SEQUENCE: 87
aagcaggagc aaagtcacat cttacattgc ggcggcat                          38

<210> SEQ ID NO 88
<211> LENGTH: 38
<212> TYPE: DNA
<213> ORGANISM: Homo sapiens

<400> SEQUENCE: 88
atgtaattcc aaagtcctcc atgacctggc ttctacct                          38

<210> SEQ ID NO 89
<211> LENGTH: 38
<212> TYPE: DNA
<213> ORGANISM: Homo sapiens

<400> SEQUENCE: 89
ctacaaattc aatgacagta gagactttgc ttttactt                          38

<210> SEQ ID NO 90
<211> LENGTH: 37
<212> TYPE: DNA
<213> ORGANISM: Homo sapiens

<400> SEQUENCE: 90
atgcaacagc aagagcagca tgactttgtt tttcctt                           37

<210> SEQ ID NO 91
<211> LENGTH: 42
<212> TYPE: DNA
<213> ORGANISM: Homo sapiens

<400> SEQUENCE: 91
gtgctgtggc ctggagcaac aaatctgact ttgcatgtgc aa                     42

<210> SEQ ID NO 92
<211> LENGTH: 38
<212> TYPE: DNA
<213> ORGANISM: Homo sapiens

<400> SEQUENCE: 92
cccaagccag ggctactgct gggtggaact ggacatgc                          38

<210> SEQ ID NO 93
<211> LENGTH: 38
<212> TYPE: DNA
<213> ORGANISM: Homo sapiens

<400> SEQUENCE: 93
ccctgtgcgg ttctgcttaa cagtagaaca ggacactt                          38

<210> SEQ ID NO 94
<211> LENGTH: 37
<212> TYPE: DNA
<213> ORGANISM: Homo sapiens

<400> SEQUENCE: 94
acatgtcaga ttctacatga ggtagaactg ttcttgt                           37

<210> SEQ ID NO 95
<211> LENGTH: 37

<212> TYPE: DNA
<213> ORGANISM: Homo sapiens

<400> SEQUENCE: 95
acaagggcag ctctgtccaa ggtagcactg ggcctgt                    37

<210> SEQ ID NO 96
<211> LENGTH: 37
<212> TYPE: DNA
<213> ORGANISM: Homo sapiens

<400> SEQUENCE: 96
cgatgtccag atgtacctca ggaaggactg gccctgg                    37

<210> SEQ ID NO 97
<211> LENGTH: 38
<212> TYPE: DNA
<213> ORGANISM: Homo sapiens

<400> SEQUENCE: 97
ccaagtcctc ctctaggaag gggtagaact ggaatttg                   38

<210> SEQ ID NO 98
<211> LENGTH: 37
<212> TYPE: DNA
<213> ORGANISM: Homo sapiens

<400> SEQUENCE: 98
gaaggtccag tgcaatgttg aatagaagtg gacatct                    37

<210> SEQ ID NO 99
<211> LENGTH: 37
<212> TYPE: DNA
<213> ORGANISM: Homo sapiens

<400> SEQUENCE: 99
agaggcccac tcctagaagg ggtagacctg gatctgg                    37

<210> SEQ ID NO 100
<211> LENGTH: 37
<212> TYPE: DNA
<213> ORGANISM: Homo sapiens

<400> SEQUENCE: 100
ccaggtccag ttctaccagc cacagatgtg agcatgt                    37

<210> SEQ ID NO 101
<211> LENGTH: 38
<212> TYPE: DNA
<213> ORGANISM: Homo sapiens

<400> SEQUENCE: 101
acaattccag ttcaagaatc ttttaaaggt ggacatgg                   38

<210> SEQ ID NO 102
<211> LENGTH: 38
<212> TYPE: DNA
<213> ORGANISM: Homo sapiens

<400> SEQUENCE: 102
gctggtgcag ctctacacgg atgcagagct ggtcctcc                   38

<210> SEQ ID NO 103

<211> LENGTH: 37
<212> TYPE: DNA
<213> ORGANISM: Homo sapiens

<400> SEQUENCE: 103
cctgggccag tgctgcttgt ccttgaaccg ggcctgg                              37

<210> SEQ ID NO 104
<211> LENGTH: 37
<212> TYPE: DNA
<213> ORGANISM: Homo sapiens

<400> SEQUENCE: 104
ggagatccag tgcgacagtc agaagaaggg gactcgg                              37

<210> SEQ ID NO 105
<211> LENGTH: 38
<212> TYPE: DNA
<213> ORGANISM: Homo sapiens

<400> SEQUENCE: 105
ctacaaattc aatgacagta gagactttgc ttttactt                             38

<210> SEQ ID NO 106
<211> LENGTH: 38
<212> TYPE: DNA
<213> ORGANISM: Homo sapiens

<400> SEQUENCE: 106
ccaggtcagg ttccggaaag aagtagaact tgacccct                             38

<210> SEQ ID NO 107
<211> LENGTH: 41
<212> TYPE: DNA
<213> ORGANISM: Homo sapiens

<400> SEQUENCE: 107
tcaagtccag ttctacgggc tctcggagaa tgacgagtgg a                         41

<210> SEQ ID NO 108
<211> LENGTH: 102
<212> TYPE: DNA
<213> ORGANISM: Homo sapiens
<220> FEATURE:
<221> NAME/KEY: CDS
<222> LOCATION: (1)..(102)
<220> FEATURE:
<221> NAME/KEY: modified_base
<222> LOCATION: (102)..(102)
<223> OTHER INFORMATION: a, c, t, g, unknown or other

<400> SEQUENCE: 108 yta gac atg agg tct atg gac ttc aag agc aac agt gct gtg gcc tgg     48
Leu Asp Met Arg Ser Met Asp Phe Lys Ser Asn Ser Ala Val Ala Trp
1               5                   10                  15 agc aac aaa tct gac ttt gca tgt gca aac gcc ttc aac aac agc att     96
Ser Asn Lys Ser Asp Phe Ala Cys Ala Asn Ala Phe Asn Asn Ser Ile
            20                  25                  30 att ccn                                                              102
Ile Pro <210> SEQ ID NO 109
<211> LENGTH: 34
<212> TYPE: PRT
<213> ORGANISM: Homo sapiens

<400> SEQUENCE: 109

Leu Asp Met Arg Ser Met Asp Phe Lys Ser Asn Ser Ala Val Ala Trp
1               5                   10                  15

Ser Asn Lys Ser Asp Phe Ala Cys Ala Asn Ala Phe Asn Asn Ser Ile
            20                  25                  30

Ile Pro

<210> SEQ ID NO 110
<211> LENGTH: 106
<212> TYPE: DNA
<213> ORGANISM: Homo sapiens

<400> SEQUENCE: 110
agacatgagg tctatggact tcaagagcaa cagtgctgtg gcctggagca acaaatctga    60
ctttgcatgt gcaaacgcct tcaacaacag cattattcca gaagac                 106

<210> SEQ ID NO 111
<211> LENGTH: 105
<212> TYPE: DNA
<213> ORGANISM: Homo sapiens

<400> SEQUENCE: 111
agacatgagg tctatggact tcaagagcaa cagtgctgtg gcctggagca acaatctgac    60
tttgcatgtg caaacgcctt caacaacagc attattccag aagac                  105

<210> SEQ ID NO 112
<211> LENGTH: 105
<212> TYPE: DNA
<213> ORGANISM: Homo sapiens

<400> SEQUENCE: 112
agacatgagg tctatggact tcaagagcaa cagtgctgtg gcctggagca acaaatcgac    60
tttgcatgtg caaacgcctt caacaacagc attattccag aagac                  105

<210> SEQ ID NO 113
<211> LENGTH: 104
<212> TYPE: DNA
<213> ORGANISM: Homo sapiens

<400> SEQUENCE: 113
agacatgagg tctatggact tcaagagcaa cagtgctgtg gcctggagca acaactgact    60 tgcatgtgc aaacgccttc aacaacagca ttattccaga agac                    104

<210> SEQ ID NO 114
<211> LENGTH: 104
<212> TYPE: DNA
<213> ORGANISM: Homo sapiens

<400> SEQUENCE: 114
agacatgagg tctatggact tcaagagcaa cagtgctgtg gcctggagca aaatctgact    60 tgcatgtgc aaacgccttc aacaacagca ttattccaga agac                    104

<210> SEQ ID NO 115
<211> LENGTH: 104
<212> TYPE: DNA
<213> ORGANISM: Homo sapiens

<400> SEQUENCE: 115
agacatgagg tctatggact tcaagagcaa cagtgctgtg gcctggagca acaaatgact    60
ttgcatgtgc aaacgccttc aacaacagca ttattccaga agac    104

<210> SEQ ID NO 116
<211> LENGTH: 104
<212> TYPE: DNA
<213> ORGANISM: Homo sapiens

<400> SEQUENCE: 116
agacatgagg tctatggact tcaagagcaa cagtgctgtg gcctggagca acatctgact    60
ttgcatgtgc aaacgccttc aacaacagca ttattccaga agac    104

<210> SEQ ID NO 117
<211> LENGTH: 103
<212> TYPE: DNA
<213> ORGANISM: Homo sapiens

<400> SEQUENCE: 117
agacatgagg tctatggact tcaagagcaa cagtgctgtg gcctggagca acaaatcctt    60
tgcatgtgca aacgccttca acaacagcat tattccagaa gac    103

<210> SEQ ID NO 118
<211> LENGTH: 102
<212> TYPE: DNA
<213> ORGANISM: Homo sapiens

<400> SEQUENCE: 118
agacatgagg tctatggact tcaagagcaa cagtgctgtg gcctggagca acatgactttt   60 gcatgtgcaa acgccttcaa caacagcatt attccagaag ac    102

<210> SEQ ID NO 119
<211> LENGTH: 99
<212> TYPE: DNA
<213> ORGANISM: Homo sapiens

<400> SEQUENCE: 119
agacatgagg tctatggact tcaagagcaa cagtgctgtg gcctggagca acaaatcgca    60
tgtgcaaacg ccttcaacaa cagcattatt ccagaagac    99

<210> SEQ ID NO 120
<211> LENGTH: 96
<212> TYPE: DNA
<213> ORGANISM: Homo sapiens

<400> SEQUENCE: 120
agacatgagg tctatggact tcaagagcaa cagtgctgtg gcctggatga ctttgcatgt    60
gcaaacgcct tcaacaacag cattattcca gaagac    96

<210> SEQ ID NO 121
<211> LENGTH: 92
<212> TYPE: DNA
<213> ORGANISM: Homo sapiens

<400> SEQUENCE: 121
agacatgagg tctatggact tcaagagcaa cagtgctgtg gcctgacttt gcatgtgcaa    60
acgccttcaa caacagcatt attccagaag ac    92

<210> SEQ ID NO 122
<211> LENGTH: 90

```
<212> TYPE: DNA
<213> ORGANISM: Homo sapiens

<400> SEQUENCE: 122
agacatgagg tctatggact tcaagagcaa cagtgctgtt ctgactttgc atgtgcaaac    60
gccttcaaca acagcattat tccagaagac                                    90

<210> SEQ ID NO 123
<211> LENGTH: 89
<212> TYPE: DNA
<213> ORGANISM: Homo sapiens

<400> SEQUENCE: 123
agacatgagg tctatggact tcaagagcaa cagtgctgtg gcctgttgca tgtgcaaacg    60
ccttcaacaa cagcattatt ccagaagac                                     89

<210> SEQ ID NO 124
<211> LENGTH: 88
<212> TYPE: DNA
<213> ORGANISM: Homo sapiens

<400> SEQUENCE: 124
agacatgagg tctatggact tcaagagcaa cagtgctgtg gcctggagca acaaatccgc    60
cttcaacaac agcattattc cagaagac                                      88

<210> SEQ ID NO 125
<211> LENGTH: 86
<212> TYPE: DNA
<213> ORGANISM: Homo sapiens

<400> SEQUENCE: 125
agacatgagg tctatggact tcaagagcaa cagtgctgtg gcctggagca acaaatccct    60
tcaacaacag cattattcca gaagac                                        86

<210> SEQ ID NO 126
<211> LENGTH: 85
<212> TYPE: DNA
<213> ORGANISM: Homo sapiens

<400> SEQUENCE: 126
agacatgagg tctatggact tcaagagcaa cagtgctgtg tttgcatgtg caaacgcctt    60
caacaacagc attattccag aagac                                         85

<210> SEQ ID NO 127
<211> LENGTH: 82
<212> TYPE: DNA
<213> ORGANISM: Homo sapiens

<400> SEQUENCE: 127
agacatgagg tctatggact tcaagagcaa cagtgctgtg gcctggagca acgccttcaa    60
caacagcatt attccagaag ac                                            82

<210> SEQ ID NO 128
<211> LENGTH: 82
<212> TYPE: DNA
<213> ORGANISM: Homo sapiens

<400> SEQUENCE: 128
agacatgagg tctatggact tcaagagcaa cagtgctgtg gcatgtgcaa acgccttcaa    60
```
caacagcatt attccagaag ac                                                    82

<210> SEQ ID NO 129
<211> LENGTH: 79
<212> TYPE: DNA
<213> ORGANISM: Homo sapiens

<400> SEQUENCE: 129
agacatgagg tctatggact tcaagagcaa cagtgctgca tgtgcaaacg ccttcaacaa          60
cagcattatt ccagaagac                                                       79

<210> SEQ ID NO 130
<211> LENGTH: 73
<212> TYPE: DNA
<213> ORGANISM: Homo sapiens

<400> SEQUENCE: 130
agacatgagg tctatggact tcaagagcaa cagtgctgca aacgccttca acaacagcat          60
tattccagaa gac                                                             73

<210> SEQ ID NO 131
<211> LENGTH: 69
<212> TYPE: DNA
<213> ORGANISM: Homo sapiens

<400> SEQUENCE: 131
agacatgagg tctatggact tcaagagcaa cagtgctgtg gcctggacaa cagcattatt          60
ccagaagac                                                                  69

<210> SEQ ID NO 132
<211> LENGTH: 64
<212> TYPE: DNA
<213> ORGANISM: Homo sapiens

<400> SEQUENCE: 132
agacatgagg tctatggact tcaagagcaa cagtgctgtg gcctggagca tttttccaga          60
agac                                                                       64

<210> SEQ ID NO 133
<211> LENGTH: 62
<212> TYPE: DNA
<213> ORGANISM: Homo sapiens

<400> SEQUENCE: 133
agacatgagg tctatggact tcaagagcaa acgccttcaa caacagcatt attccagaag          60
ac                                                                         62

<210> SEQ ID NO 134
<211> LENGTH: 23
<212> TYPE: DNA
<213> ORGANISM: Homo sapiens

<400> SEQUENCE: 134
acaacagcat tattccagaa gac                                                  23

<210> SEQ ID NO 135
<211> LENGTH: 106
<212> TYPE: DNA
<213> ORGANISM: Homo sapiens

<400> SEQUENCE: 135
agacatgagg tctatggact tcaagagcaa cagtgctgtg gcctggagca acaaatctga        60
ctttgcatgt gcaaacgcct tcaacaacag cattattcca gaagac                      106

<210> SEQ ID NO 136
<211> LENGTH: 106
<212> TYPE: DNA
<213> ORGANISM: Homo sapiens

<400> SEQUENCE: 136
agacatgagg tctatggact tcaagagcaa cagtgctgtg gcctggagca acaaaatctg        60
actttgcatg tgcaaacgcc ttcaacaaca gcattattcc agaaga                       106

<210> SEQ ID NO 137
<211> LENGTH: 106
<212> TYPE: DNA
<213> ORGANISM: Homo sapiens

<400> SEQUENCE: 137
agacatgagg tctatggact tcaagagcaa cagtgctgtg gcctggagca acaaatcaat        60
ctgactttgc atgtgcaaac gccttcaaca acagcattat tccaga                       106

<210> SEQ ID NO 138
<211> LENGTH: 103
<212> TYPE: DNA
<213> ORGANISM: Homo sapiens

<400> SEQUENCE: 138
agacatgagg tctatggact tcaagagcaa cagtgctgtg gcctggagca acaattgact        60
ttgcatgtgc aaacgccttc aacaacagca ttattccaga aga                          103

<210> SEQ ID NO 139
<211> LENGTH: 103
<212> TYPE: DNA
<213> ORGANISM: Homo sapiens

<400> SEQUENCE: 139
agacatgagg tctatggact tcaagagcaa cagtgctgtg gcctggagca acaaaggact        60
ttgcatgtgc aaacgccttc aacaacagca ttattccaga aga                          103

<210> SEQ ID NO 140
<211> LENGTH: 103
<212> TYPE: DNA
<213> ORGANISM: Homo sapiens

<400> SEQUENCE: 140
agacatgagg tctatggact tcaagagcaa cagtgctgtg gcctggagca acagatgact        60
ttgcatgtgc aaacgccttc aacaacagca ttattccaga aga                          103

<210> SEQ ID NO 141
<211> LENGTH: 94
<212> TYPE: DNA
<213> ORGANISM: Homo sapiens

<400> SEQUENCE: 141
agacatgagg tctatggact tcaagagcaa cagtgctgtg gcctggcctg tttgcatgtg        60
caaacgcctt caacaacagc attattccag aaga                                    94

<210> SEQ ID NO 142

```
<211> LENGTH: 93
<212> TYPE: DNA
<213> ORGANISM: Homo sapiens

<400> SEQUENCE: 142
agacatgagg tctatggact tcaagagcaa cagtgctgtg gctgtgctgt ttgcatgtgc    60
aaacgccttc aacaacagca ttattccaga aga                                93

<210> SEQ ID NO 143
<211> LENGTH: 90
<212> TYPE: DNA
<213> ORGANISM: Homo sapiens

<400> SEQUENCE: 143
agacatgagg tctatggact tcaagagcaa cagtgctgtg gcctggagct cttgtgcaaa    60
cgccttcaac aacagcatta ttccagaaga                                     90
```

TARGETED DISRUPTION OF T CELL RECEPTOR GENES USING ENGINEERED ZINC FINGER PROTEIN NUCLEASES

CROSS-REFERENCE TO RELATED APPLICATIONS

The present application is a continuation of U.S. patent application Ser. No. 12/927,292, filed Nov. 10, 2010, which claims the benefit of U.S. Provisional Application Nos. 61/280,863, filed Nov. 10, 2009; 61/404,064, filed Sep. 27, 2010 and 61/404,685, filed Oct. 6, 2010, the disclosures of which are hereby incorporated by reference in their entireties.

STATEMENT OF RIGHTS TO INVENTIONS MADE UNDER FEDERALLY SPONSORED RESEARCH

Not applicable.

TECHNICAL FIELD

The present disclosure is in the field of genome modification of human cells, including lymphocytes and stem cells.

BACKGROUND

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; 20060188987; 2008015996, and International Publication WO 2007/014275, the disclosures of which are incorporated by reference in their entireties for all purposes.

The T cell receptor (TCR) is an essential part of the selective activation of T cells. Bearing some resemblance to an antibody, the TCR is typically made from two chains, α and β, which co-assemble to form a heterodimer. The antibody resemblance lies in the manner in which a single gene encoding a TCR chain is put together. TCR chains are composed of two regions, a C-terminal constant region and an N-terminal variable region. The genomic loci that encode the TCR chains resemble antibody encoding loci in that the TCR α gene comprises V and J segments, while the β chain locus comprises D segments in addition to V and J segments. During T cell development, the various segments recombine such that each T cell has a unique TCR structure, and the body has a large repertoire of T cells which, due to their unique TCR structures, are capable of interacting with unique antigens displayed by antigen presenting cells. Additionally, the TCR complex makes up part of the CD3 antigen complex on T cells.

During T cell activation, the TCR interacts with antigens displayed on the major histocompatability complex (MHC) of an antigen presenting cell. Recognition of the antigen-MHC complex by the TCR leads to T cell stimulation, which in turn leads to differentiation of both T helper cells (CD4+) and cytotoxic T lymphocytes (CD8+) in memory and effector lymphocytes. These cells then can expand in a clonal manner to give an activated subpopulation within the whole T cell population capable of reacting to one particular antigen.

Cytotoxic T lymphocytes (CTLs) are thought to be essential in killing tumor cells. These cells typically are able to induce apoptosis in cancer cells when the cancer cell displays some antigen on its surface that was previously displayed on the MHC by an antigen presenting cell. Normally, following action against target cells, CTLs will apoptose when the cellular threat is cleared, with a subset of lymphocytes remaining that will further differentiate into memory T cells to persist in case the body is exposed to the antigen again. The pool of memory lymphocytes is possibly highly heterogeneous. Recently, two types of memory T-cells have been identified: effector memory T-cells (CD45RA- CCR7-, CD62L-) and central memory T-cells that are CD45RA negative cells characterized by the expression of CCR7 and CD62L, two molecules required for homing in T-cell areas of secondary lymphoid organs. Upon antigenic stimulation, central memory T-cells produce low levels of effector cytokines such as IL-4 and IFN-γ, but high levels of IL-2, which is able to sustain their rapid and consistent proliferation. Upon antigen encounter central memory T-cells undergo: 1) proliferation, resulting in an auto-regenerative process, aimed at increasing their pool, and 2) differentiation, resulting in the generation of effector memory T-cells, which are characterized by a low proliferative potential but are able to migrate to inflamed non-lymphoid tissues and mediate the effector phase of the immune response. Protocols enabling gene transfer into T lymphocytes, while preserving their central memory functional phenotype have been developed (see European Patent Publication No EP1956080, Kaneko et al., 2009 *Blood* 113(5):1006-15).

However, some tumor cells are able to escape surveillance by the immune system, perhaps through mechanisms such as poor clonal expansion of certain CTL subsets expressing the relevant TCR, and localized immune suppression by cancer cells (see Boon et al, (2006) *Annu Rev Immunol.* 24:175-208). The notion of a cancer vaccine is built upon the idea of using these cancer specific antigens to stimulate and expand the CTLs that express the appropriate TCR in vivo, in an attempt to overcome immune escape, however, these cancer vaccines have yet to show any marked success. In fact, an analysis done in 2004 examined 765 metastatic cancer patients that had been treated in over 35 different cancer vaccine trials, where an overall response was observed in only 3.8% of patients (see Rosenberg et at (2004) *Nat. Med.* 10(9): 909-915).

Adoptive immunotherapy is the practice of achieving highly specific T cell stimulation of a certain subpopulation of CTLs that possess a high-avidity TCR to the tumor antigen, stimulating and expanding them ex vivo, and then introducing them into the patient. Adoptive immunotherapy is particularly effective if native lymphocytes are removed from the patient before the infusion of tumor-specific cells. The idea behind this type of therapy is that if the introduced high-avidity CTLs are successful, once the tumor has been cleared, some of these cells will become memory T cells and will persist in the patient in case the cancer reappears. In 2002, a study was completed demonstrating regression of metastatic melanoma in patients that were treated under a regime of adoptive immunotherapy following immunodepletion with cyclophosphamide and fludarabine (Dudley et al, (2002) *Science,* 298(5594): 850-854). Response rate was even higher if adoptive immunotherapy was preceded by total body irradiation (Dudley et at 2008 *J Clin Oncol.* 26(32):5233-9).

However, adoptive immunotherapy has not been successful when the T cells of interest containing high avidity TCRs cannot be readily expanded. In addition, it is often difficult to identify and isolate T cells with therapeutic value from cancer patients because tumor antigens are often self-antigens, against which the patient's immune system is made tolerant through mechanisms of deletion or anergy of those T cell clones with the highest avidity. Thus, transfer of genes encoding high avidity TCRs into patient derived T cells has been proposed and demonstrated (see Rubenstein et al, (2003) *J of Immunology* 170: 1209-1217). More recently, using a mouse model of malignant melanoma, a statistically significant decrease in tumor mass was found following introduction of normal lymphocytes that had been transduced with retroviral vectors carrying human TCR genes specific for the gp-100 melanoma antigen (Abad et al, (2008) *J Immunother.* 31(1): 1-6) TCR gene therapy is also described in Morgan et al, 2006 *Science* 314(5796):126-9 and Burns et al, 2009 *Blood* 114(14):2888-99.

However, transfer of any TCR transgenes into host T cells carries with it the caveats associated with most gene transfer methods, namely, unregulated and unpredictable insertion of the TCR transgene expression cassette into the genome, often at a low level. Such poorly controlled insertion of the desired transgene can result in effects of the transgene on surrounding genes as well as silencing of the transgene due to effects from the neighboring genes. In addition, the endogenous TCR genes that are co-expressed in the T cell engineered with the introduced TCR transgene could cause undesired stimulation of the T cell by the antigen recognized by the endogenous TCR, undesired stimulation of the T cell by unintended antigens due to the mispairing of the TCR transgene with the endogenous TCR subunits creating a novel TCR complex with novel recognition properties, or can lead to suboptimal stimulation against the antigen of interest by the creation of inactive TCRs due to heterodimerization of the transgene encoded TCR subunits with the endogenous TCR proteins. In fact, the risk of severe autoimmune toxicity resulting from the formation of self-reactive TCR from mispairing of endogenous and exogenous chains has been recently highlighted in a murine model (Bendle et al., (2010) *Nature Medicine* 16:565-570) and in human cells (van Loenen et al., (2010) *Proc Natl Acad Sci USA* 107:10972-7). Additionally, the tumor-specific TCR may be expressed at suboptimal levels on the cell surface, due to competition with the endogenous and mispaired TCR for the CD3 molecules, required to express the complex on the cell surface.

Wilms tumor antigen (WT1 antigen) is a transcription factor normally expressed in embryonic cells. After birth, its expression is limited to only a few cell types including hematopoietic stem cells. However, it has been found to be overexpressed in many types of leukemias and solid tumors (see Inoue et at (1997) *Blood* 89: 1405-1412) and may contribute to a lack of growth control in these cells. Due to the low expression of WT1 in normal tissues, its expression on cancer cells makes it an attractive target for T-cell mediated therapy. TCR variants with increased avidity to WT1 containing a modified cysteine to discourage mispairing between the endogenous TCR subunits and the transgene TCRs have been transduced into primary T cells and tested for functionality (Kuball et at (2007) *Blood* 109(6):2331-8). The data demonstrated that while T cells that had been freshly transduced with the WT1-TCR variants had an increased antigen response as compared to those transduced with a wildtype TCR domain, after several rounds of stimulation with the WT1 antigen, this improved antigen responsiveness was lost (see Thomas et at (2007) *J of Immunol* 179 (9): 5803-5810). It was concluded that even with the trans-gene-specific cysteine modification, mispairing with the endogenous TCR peptides may play a role in reducing anti-WT1 avidity seen in cells transduced with the WT1-specific TCRs.

Thus, there remains a need for compositions that can introduce desired TCR transgenes into a known chromosomal locus. In addition, there is a need for methods and compositions that can selectively knock out endogenous TCR genes.

SUMMARY

Disclosed herein are compositions and methods for partial or complete inactivation or disruption of a TCR gene and compositions and methods for introducing and expressing to desired levels of exogenous TCR transgenes into T lymphocytes, after or simultaneously with the disruption of the endogenous TCR.

In one aspect, provided herein are zinc finger nucleases (ZFNs) that cleave a TCR gene. In certain embodiments, the ZFNs bind to target sites in a human TCR α gene and/or target sites in a human TCR β gene. In some embodiments, cleavage within the TCR gene(s) with these nucleases results in permanent disruption (e.g., mutation) of the TCR α and/or β gene(s). The zinc finger proteins may include 1, 2, 3, 4, 5, 6 or more zinc fingers, each zinc finger having a recognition helix that binds to a target subsite in the target gene. In certain embodiments, the zinc finger proteins comprise 4 or 5 or 6 fingers (designated F1, F2, F3, F4, F5 and F6 and ordered F1 to F4 or F5 or F6 from N-terminus to C-terminus) and the fingers comprise the amino acid sequence of the recognition regions shown in Table 5 and Table 6 and/or recognize the target sites shown in Tables 5 and 6.

Any of the proteins described herein may further comprise a cleavage domain and/or a cleavage half-domain (e.g., a wild-type or engineered FokI cleavage half-domain). Thus, in any of the ZFNs described herein, the nuclease domain may comprise a wild-type nuclease domain or nuclease half-domain (e.g., a FokI cleavage half domain). In other embodiments, the ZFNs comprise engineered nuclease domains or half-domains, for example engineered FokI cleavage half domains that form obligate heterodimers. See, e.g., U.S. Patent Publication No. 20080131962.

In another aspect, the disclosure provides a polynucleotide encoding any of the proteins described herein. Any of the polynucleotides described herein may also comprise sequences (donor or patch sequences) for targeted insertion into the TCR α and/or the TCR β gene. In yet another aspect, a gene delivery vector comprising any of the polynucleotides described herein is provided. In certain embodiments, the vector is an adenoviral vector (e.g., an Ad5/F35 vector) or a lentiviral vector (LV) including integration competent or integration-defective lentiviral vectors. Thus, also provided herein are adenoviral (Ad) vectors or LVs comprising a sequence encoding at least one zinc finger nuclease (ZFN) and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments the vector is pseudo-typed with a VSV-G envelope, or with other envelopes. In additional embodiments, the target gene is the human TCR α gene. In certain embodiments, the target gene is the human TCR β gene. The vectors described herein may also comprise donor sequences. In additional embodiments, the donor sequences comprise human TCR genes that are specific for an MHC/antigen complex of interest. In some embodiments, the donor sequences may comprise the human TCR α and/or the human TCR β genes that are specific for an MHC/antigen complex of interest. In certain embodiments, a single vector comprises sequences encoding one or more ZFNs and the donor sequence(s). In other embodiments, the donor sequence(s) are contained in a first vector and the ZFN-encoding sequences are present in a second vector. In further embodiments, the ZFN-encoding sequences are present in a first vector and the TCR α gene of interest is present in a second vector and the TCR β gene of interest is present in a third vector. In some embodiments, the TCR genes of interest are inserted into the location of the endogenous TCR genes, and in other embodiments the TCR genes of interest are inserted into randomly selected loci, or into a separate locus after genome-wide delivery. In some embodiments, the separate locus for TCR transgene insertion is the PPP1R12C locus (also known as AAVS1, see U.S Patent Publication Number 20080299580). In other embodiments, the TCR transgene is inserted into a CCR-5 locus.

In yet another aspect, the disclosure provides an isolated cell comprising any of the proteins, polynucleotides and/or vectors described herein. In certain embodiments, the cell is selected from the group consisting of a stem/progenitor cell, a T-cell (e.g., CD4$^+$ T-cell). In a still further aspect, the disclosure provides a cell or cell line which is descended from a cell or line comprising any of the proteins, polynucleotides and/or vectors described herein, namely a cell or cell line descended (e.g., in culture) from a cell in which TCR has been inactivated by one or more ZFNs and/or in which a TCR-encoding donor polynucleotide has been stably integrated into the genome of the cell. Thus, descendants of cells as described herein may not themselves comprise the proteins, polynucleotides and/or vectors described herein, but, in these cells, a TCR gene is inactivated and/or a TCR-encoding donor polynucleotide is integrated into the genome and/or expressed.

In another aspect, described herein are methods of inactivating a TCR gene in a cell by introducing one or more proteins, polynucleotides and/or vectors into the cell as described herein. In any of the methods described herein the ZFNs may induce targeted mutagenesis, targeted deletions of cellular DNA sequences, and/or facilitate targeted recombination at a predetermined chromosomal locus. Thus, in certain embodiments, the ZFNs delete or insert one or more nucleotides of the target gene. In some embodiments the TCR gene is inactivated by ZFN cleavage followed by non-homologous end joining. In other embodiments, a genomic sequence in the target gene is replaced, for example using a ZFN (or vector encoding said ZFN) as described herein and a "donor" sequence that is inserted into the gene following targeted cleavage with the ZFN. The donor sequence may be present in the ZFN vector, present in a separate vector (e.g., Ad or LV vector) or, alternatively, may be introduced into the cell using a different nucleic acid delivery mechanism.

In another aspect, methods of using the zinc finger proteins and fusions thereof for mutating a TCR gene and/or inactivating TCR function in a cell or cell line are provided. Thus, a method for inactivating a TCR gene in a human cell is provided, the method comprising administering to the cell any of the proteins or polynucleotides described herein.

In yet another aspect, the disclosure provides a method for treating or preventing cancer, infections, autoimmune disorders, and/or graft-versus-host disease (GVHD) in a subject, the method comprising: (a) introducing, into a cell (e.g., lymphocyte, stem cell, progenitor cell, etc.), a first nucleic acid encoding a first polypeptide, wherein the first polypeptide comprises: (i) a zinc finger DNA-binding domain that is engineered to bind to a first target site in a TCR gene; and (ii) a cleavage domain; under conditions such that the polypeptide is expressed in the cell, whereby the polypeptide binds to the target site and cleaves the endogenous TCR gene; and (b) introducing, into the cell, a second nucleic acid encoding a second polypeptide, wherein the second polypeptide comprises: (i) a zinc finger DNA-binding domain that is engineered to bind to a second target site in a TCR gene; and (ii) a cleavage domain; under conditions such that the polypeptide is expressed in the cell, whereby the polypeptide binds to the target site and cleaves the endogenous TCR gene; and (c) introducing into the cell a third nucleic acid comprising a nucleic acid encoding a TCR gene or TCR genes, specific for a tumor specific antigen in an MHC complex, such that the third nucleic acid is introduced into the endogenous TCR gene and the cell with the introduced third nucleic acid treats or prevents. In certain embodiments, steps (a)-(c) are performed ex vivo and the method further comprises, following step (c), the step of introducing the cell into the subject. In certain embodiments, the third nucleic acid encoding the TCR gene(s) is expressed under the control of bi-directional promoters (e.g., PGK, EF1α, etc.). In other embodiments, the TCR gene(s) are expressed from bicistronic cassettes (e.g., using viral 2A peptides or an IRES sequence) or by multiple LVs expressing different TCR genes under monodirectional promoters. In certain embodiments, the cell is selected from the group consisting of a stem/progenitor cell, or a T-cell.

In any of the methods describes herein, the first nucleic acid may further encode a second polypeptide, wherein the second polypeptide comprises: (i) a zinc finger DNA-binding domain that is engineered to bind to a second target site in the TCR gene; and (ii) a cleavage domain; such that the second polypeptide is expressed in the cell, whereby the first and second polypeptides bind to their respective target sites and cleave the TCR gene.

In another aspect, the disclosure also provides a method for treating or preventing cancer in a subject, the method comprising: (a) introducing, into a cell, a first nucleic acid encoding a first polypeptide, wherein the first polypeptide comprises: (i) a zinc finger DNA-binding domain that is engineered to bind to a first target site in a TCR gene; and (ii) a cleavage domain; under conditions such that the polypeptide is expressed in the cell, whereby the polypeptide binds to the target site and cleaves the endogenous TCR; and (b) introducing, into a cell, a second nucleic acid encoding a second polypeptide, wherein the second polypeptide comprises: (i) a zinc finger DNA-binding domain that is engineered to bind to a first target site in a safe harbor locus (e.g., PPP1R12C, CCR5); and (ii) a cleavage domain; under conditions such that the polypeptide is expressed in the cell, whereby the polypeptide binds to the target site and cleaves in the safe harbor locus (e.g., PPP1R12C, CCR5) and (c) introducing into the cell a third nucleic acid comprising a donor nucleic acid encoding a TCR gene or TCR genes specific for a tumor specific antigen in an MHC complex; and (d) introducing the cell into the subject. The nucleic acids comprising the TCR specific ZFN may be introduced simultaneously with the ZFN specific for the safe-harbor locus and the donor nucleic acid molecule, or the nucleic acid encoding the TCR-specific ZFN may be introduced into the cell in a first step, and then the safe harbor locus (e.g., PPP1R12C, CCR5)-specific ZFNs and the donor nucleic acid molecule may be introduced in a second step.

The disclosure also provides a method of preventing or treating a cancer in a subject comprising introducing, into a subject, a viral delivery particle wherein the viral delivery particle comprises (a) a first nucleic acid encoding a first polypeptide, wherein the first polypeptide comprises: (i) a zinc finger DNA-binding domain that is engineered to bind to a first target site in a TCR gene; and (ii) a cleavage domain; under conditions such that the polypeptide is expressed in the cell, whereby the polypeptide binds to the target site and cleaves the endogenous TCR; and (b) a second nucleic acid encoding a second polypeptide, wherein the second polypeptide comprises: (i) a zinc finger DNA-binding domain that is engineered to bind to a first target site in a safe harbor locus (e.g., PPP1R12C, CCR5); and (ii) a cleavage domain; under conditions such that the polypeptide is expressed in the cell, whereby the polypeptide binds to the target site and cleaves the safe harbor locus (e.g., PPP1R12C, CCR5); and (c) a third nucleic acid encoding a third polypeptide, wherein the third polypeptide comprises: (i) a zinc finger DNA-binding domain that is engineered to bind to a second target site in a safe harbor locus (e.g., PPP1R12C, CCR5); and (ii) a cleavage domain; under conditions such that the polypeptide is expressed in the cell, whereby the polypeptide binds to the target site and cleaves at the safe harbor locus (e.g., PPP1R12C, CCR5); and (d) a third nucleic acid comprising a donor nucleic acid encoding a TCR gene or TCR genes specific for a tumor specific antigen in an MHC complex; such that the endogenous TCR gene is cleaved and rendered inactive, and the safe harbor gene (e.g., PPP1R12C, CCR5) is cleaved and the TCR gene specific for a tumor specific antigen in an MHC complex becomes inserted into the endogenous TCR gene. In certain embodiments, the method further comprises, following step (d), the step of introducing the cell into the subject.

In any of the methods described herein, a viral delivery particle can be used to deliver one or more of the polynucleotides (ZFN-encoding and/or donor polynucleotides). Furthermore, in any of the methods and compositions described herein, the cell can be, for example, a stem/progenitor cell (e.g., a CD34+ cell), or a T-cell (e.g., a CD4+ cell).

Furthermore, any of the methods described herein can be practiced in vitro, in vivo and/or ex vivo. In certain embodiments, the methods are practiced ex vivo, for example to modify PBMCs, e.g., T-cells, to make them specific for a tumor antigen/MHC complex of interest to treat a tumor in a subject. Non-limiting examples of cancers that can be treated and/or prevented include lung carcinomas, pancreatic cancers, liver cancers, bone cancers, breast cancers, colorectal cancers, leukemias, ovarian cancers, lymphomas, brain cancers and the like.

BRIEF DESCRIPTION OF THE DRAWINGS

FIG. 1A depicts a diagram of the genes encoding a codon-optimized, cysteine-modified TCR specific for an HLA-A2-restricted peptide from the Wilms tumor antigen 1 (WT1) cloned into a third generation lentiviral vector (LV) under the control of a bi-directional PGK or E1α promoter. See, Amendola et at (2005) Nature Biotechnology 23(1): 108-116 and U.S. Patent Publication No US2006200869. FIG. 1B is a graph depicting a time course of Vβ21 TCR expression in lentivirus transduced CD8+ cells cultured in the presence of 5 ng/ml of IL7 and IL15. Vβ21 relative fluorescence intensity (RFI) was calculated as the ratio of the mean fluorescence intensity (MFI) of Vβ21 measured in PGK-WT1 (open squares) or EF1α-WT1 ("X") genetically modified lymphocytes/the MFI of Vβ21 measured in T cells naturally expressing Vβ21.

FIGS. 2A through 2C, are graphs depicting results of cells transduced with TCR constructs. FIG. 2A depicts induction of γIFN production by stimulation of the cells with WT1+/HLA A2-K562 cells (the indicated primary AML or K562 cells (right most bar in graph)) transduced with vectors expressing the transgenic TCRs either from the PGK/mCMV dual promoter combination (left side group of 4 bars) or the EF1α/mCMV dual promoter (right side group of 4 bars) following exposure to WT1+HLA-A2+ or WT1+HLA-A2− (negative control) primary leukemic blasts from AML patients (designated as AML1 (left most bar), AML2 (second bar from the left) and AML3 (third bar from the left)). FIGS. 2B and 2C demonstrate the percent killing of the leukemic blasts from AML1 and AML2 (solid lines, closed circles) by the TCR modified cells. Dotted lines represent residual killing of the leukemic blasts by the TCR modified cells in the presence of an excess of cold (not labeled) HLA-A2 target cells, loaded with the WT1 proper peptide.

FIGS. 3A and 3B demonstrate the increase in the percentage of GFP positive cells in relation to the amount of Ad5/F35 CCR5-specific ZFN (FIG. 3A) or Ad5/F35 AAVS1-specific ZFN (FIG. 3B) and -IDLV GFP donor DNA cassette used.

FIG. 4A depicts a cassette containing WT1-specific TCR-α and TCR-β donor molecules and shows the regions of homology to the CCR5 integration site. FIG. 4B depicts the genomic arrangement of the two TCR-β constant regions in K562 cells (TRBC1 and TRBC2).

FIGS. 6A and 6B, depict percent modification for TCR-α specific ZFNs in K562 cells as measured by a Cel-I assay. FIG. 6A depicts the results from a Cel-I assay on cells where the ZFNs were targeted to Exon 1. FIG. 6B depicts the results of a Cel I mismatch assay where the ZFNs were targeted to Exon 3. "GFP" indicates cells tranduced with GFP only vectors. Percent alteration (NHEJ) is indicated at the bottom of the lanes.

FIGS. 7A through 7F, depict ZFN-mediated cleavage of TCR-β. Untransduced and transduced Jurkat cells using the TCR-β specific ZFN pair 16783 and 16787 at two concentrations of vector demonstrated the loss of CD3 signal at the cell surface (from 2.7% CD3(−) to 20.2% CD3(−) (see Example 6). FIGS. 7A and 7B show the results of Cel-I assays at the TRBC1 (FIG. 7A) and the TRBC2 (FIG. 7B) locus in Jurkat cells and demonstrate that cleavage has occurred. The measured % gene modification is indicated at the bottom of each lane. FIG. 7C is a graph depicting that sorted CD3− primary human lymphocytes can survive in the presence of IL7 and IL15. "UT" indicates untreated cells. FIG. 7D shows the percent modification (NHEJ), as assayed by the Cel-I assay observed in the primary T-cell cell pools treated with TCR-beta specific ZFNs. "Bulk" indicates percent of NHEJ observed for the ZFN treated cell pool, while CD3+ or CD3− shows the NHEJ observed for cells that sorted either as CD3+ or CD3−. "UT" indicates cells that were not treated. The percent NHEJ detected by the assay is indicated at the bottom of the lanes. FIG. 7E is a graph depicting percent CD3− cells and demonstrates the persistence of CD3− cells over time (percent of CD3− cells stays fairly constant even up to 45 days) in cells treated with increasing concentrations of ZFNs. FIG. 7F is a graph depicting that CD3− cells have lost CD3 functionality since they do not appear to divide in response to non-specific mitogens.

FIGS. 9A through 9C, depict expression of Vβ21 TCR. FIG. 9A depicts Vβ21 TCR expression (upper histogram) and $WT1_{126-434}$ pentamer binding (lower histogram) in $CD8^+$ TCR β chain disrupted and WT1 transduced cells that have been sorted for CD3+ signal (TCR-β-edited), unedited WT1 LV transduced cells (TCR-transferred), and untransduced lymphocytes treated with the same culture conditions. FIG. 9B shows a time course of surface expression of Vβ21 TCR. Average+SD (n=2) of Vβ21 RFI is represented. RFI is calculated from the ratio of the MFI of Vβ21 measured in $CD8^+$ TCR-edited (open triangle) or TCR-transferred (dark circle) lymphocytes/the MFI of Vβ21 measured in $CD8^+$ T cells naturally expressing Vβ21. FIG. 9C depicts the results of a cytotoxicity assay with TCR-edited and TCR-transferred cells. Functional activity is measured by a $^{51}$Chromium release assay for lysis of labeled T2 cells pulsed with increasing concentrations of the $WT1_{126-134}$ HLA-A2 restricted peptide, or with the irrelevant CMV-derived $pp65_{495-503}$ HLA-A2 restricted peptide (10 μM) as negative control, at an Effector/Target (E/T) ratio of 12. Results are represented as average+SD of % of lysis (**, p<0.01, *, p<0.05 with Mann-Whitney test, TCR-edited n=6, TCR-transferred n=4).

FIG. 12A depicts a diagram of the human locus encoding the TCR alpha, total length 18 kb; TRAV, variable region genes, TRAD, diversity region genes, TRAC, constant region gene. Displayed above the scheme of the locus are the genomic DNA sequences in TRAC targeted by each TRAC-ZFN. FIG. 12A discloses the protein sequence as SEQ ID NO: 109 and the DNA sequence of SEQ ID NO: 108. FIG. 12B depicts down-regulation of cell surface CD3 expression measured by flow cytometry in primary human lymphocytes stimulated with baCD3/CD28, cultured with 5 ng/ml IL-7, 5 ng/ml IL-15, and exposed to TRAC-ZFN IDLVs. The percent of CD3(−) cells is plotted. UT, Untransduced cells. Sorted CD3(−) cells were transduced with WT1-α OFP-LV resulting in expression of CD3 on transduced lymphocytes. FIG. 12C depicts a gel showing the level of targeted gene disruption measured by the Cel-I assay in primary lymphocytes exposed to TRAC-ZFN. The higher migrating product indicating wild type (w/t) gene is shown. Lower migrating products (NHEJ) indicate ZFN-directed gene disruption. "UT" refers to untransduced cells.

FIG. 13 depicts partial sequence of the genomic TRAC ZFN target site in ZFN-treated human lymphocytes was amplified, cloned and sequenced to confirm ZFN-induced modification. Sequence alignment revealed several ZFN-induced deletions and insertions (indels) within the target region. The left column indicates the number of clones retrieved while the right column indicates the number of deleted or inserted nucleotides. FIG. 13 discloses SEQ ID NOS 110-143, respectively, in order of appearance.

FIG. 16C shows similar results where allogenic PBMC were used as target. All assays were performed at a stimulator/responder ratio of 1:1. The number of specific spots is shown on the y axis as the number of spots produced in the presence of stimulators minus the number of spots produced by effectors alone. *=p<0.05, =p<0.01, *=p<0.001.

FIG. 17 depicts analysis for off-target cleavage by TRAC-specific ZFNs. The 15 most likely potential off target sites for the TRAC-specific ZFNs (identified by in silicio analysis) were analyzed following ZFN treatment for cleavage by the Cel-I mismatch assay. Each potential off target site was analyzed in 5 samples: untransduced samples (UT), samples that were TRAC negative following TRAC-specific ZFN treatment and sorting (TRAC neg), cells that were TRAC and TRBC negative following sequential treatment with TRAC-specific ZFNs, the TRAC transgene and TRBC-specific ZFNs with sequential rounds of sorting (Double Neg), cells that were negative for the endogenous TRAC and TRBC loci following ZFN treatment as well as modified to comprise non-wild type TRAC and TRBC transgenes (Complete Edited), or TRBC negative following treatment with TRBC-specific ZFNs alone and sorting (TRBC Neg). Potential off target sites are as labeled in Table 13.

DETAILED DESCRIPTION

Figure 1A:
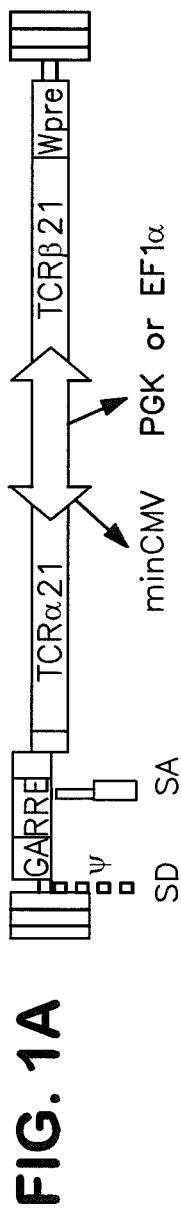
FIGS. 1A and 1B, depict construction and expression of a Wilms tumor antigen (WT1) specific lentiviral vector.

Disclosed herein are zinc finger nucleases (ZFNs) targeting a TCR gene (TCR-ZFNs). These ZFNs efficiently generate a double strand break (DSB), for example at a predetermined site in a TCR coding region. ZFN-mediated introduction of a site-specific double strand break (DSB) in genes that encode for the TCR gene can result in the specific and permanent disruption of the endogenous TCR complex in human cells, including human T cells. These cells can be selected from a pool by selecting for CD3(−) cells, and culturing them on IL7 and IL15. In addition, disclosed herein are methods and compositions for the replacement of the endogenous TCR genes with TCR transgenes of one's choice, either via random integration or by site directed targeted integration.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 20050064474 and 20060188987 and U.S. Provisional Application No. 60/808,486 (filed May 25, 2006), incorporated herein by reference in their entireties.

"Chromatin" is the nucleoprotein structure comprising the cellular genome. Cellular chromatin comprises nucleic acid, primarily DNA, and protein, including histones and nonhistone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

A "safe harbor locus" is a location within a genome that can be used for integrating exogenous nucleic acids. The addition of exogenous nucleic acids into these safe harbor loci does not cause any significant effect on the growth of the host cell by the addition of the DNA alone. Non-limiting examples of safe harbor loci include the PPP1R12C locus (also known as AAVS1, see U.S Patent Publication Number 20080299580) and the CCR5 locus (see U.S. Patent Publication Number 20080159996).

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eucaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Nucleases

Described herein are nucleases (e,g., ZFNs or TAL nucleases) that can be used for inactivation of a TCR gene The nuclease may be naturally occurring or may be a chimera of a DNA-binding domain and a cleavage domain. It will be apparent that within the chimera, the component DNA-binding and cleavage domains may both be naturally occurring, may both be non-naturally occurring or one may be naturally occurring and the other may be non-naturally occurring. Thus, any nuclease can be used in the methods disclosed herein. For example, naturally-occurring homing endonucleases and meganucleases have very long recognition sequences, some of which are likely to be present, on a statistical basis, once in a human-sized genome. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66. Thus, any naturally occurring or engineered nuclease having a unique target site can be used in the methods described herein.

A. DNA-Binding Domains

The nucleases described herein typically include a DNA-binding domain and a cleavage domain. Any DNA-binding domain can be used in the practice of the present invention.

In certain embodiments, zinc finger binding domains that are engineered to bind to a sequence of choice are employed. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in related to U.S. Publication Nos. 20030232410; 20050208489; 2005064474; 20050026157; 20060188987; International Publication WO 07/014275; U.S. patent application Ser. No. 10/587,723 (filed Jul. 27, 2006); Ser. No. 11/493,423 (filed Jul. 26, 2006), the disclosures of which are incorporated by reference in their entireties for all purposes.

The zinc finger nucleases described herein bind in a TCR gene. Tables 5 and 6(see Example 4) describes a number of zinc finger binding domains that have been engineered to bind to nucleotide sequences in the human TCR gene. Each row describes a separate zinc finger DNA-binding domain. The DNA target sequence for each domain is shown in the first column (DNA target sites indicated in uppercase letters; non-contacted nucleotides indicated in lowercase), and the second through fifth columns show the amino acid sequence of the recognition region (amino acids −1 through +6, with respect to the start of the helix) of each of the zinc fingers (F1 through F4 or F5 or F6) in the protein. Also provided in the first column is an identification number for each protein.

As described below, in certain embodiments, a four- or five-finger binding domain as shown in Tables 5 and 6 is fused to a cleavage half-domain, such as, for example, the cleavage domain of a Type IIs restriction endonuclease such as FokI. A pair of such zinc finger/nuclease half-domain fusions are used for targeted cleavage, as disclosed, for example, in U.S. Patent Publication No. 20050064474 (application Ser. No. 10/912,932).

For targeted cleavage, the near edges of the binding sites can separated by 5 or more nucleotide pairs, and each of the fusion proteins can bind to an opposite strand of the DNA target.

In addition, domains from these naturally occurring or engineered nucleases can also be isolated and used in various combinations. For example, the DNA-binding domain from a naturally occurring or engineered homing endonucleases or meganuclease can be fused to a heterologous cleavage domain or half domain (e.g., from another homing endonuclease, meganuclease or TypeIIS endonuclease). These fusion proteins can also be used in combination with zinc finger nucleases described above.

In some embodiments, the DNA binding domain is an engineered domain from a TAL effector protein derived from the plant pathogen *Xanthomonas* (see Boch et al, (2009) *Science* 326: 1509-1512 and Moscou and Bogdanove, (2009) Science326: 1501). See, also, U.S. Pat. No. 8,586, 526.

The nucleases described herein can be targeted to any sequence in any TCR genomic sequence.

B. Cleavage Domains

The nucleases also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in certain embodiments, the mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of U.S. Patent Publication No. 2008/0131962, the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

The engineered cleavage half-domains described herein may be obligate heterodimer mutants in which aberrant cleavage is minimized or abolished. See, e.g., Example 1 of WO 07/139898. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Publication No. 20110201055).

Alternatively, the FokI nuclease domain variant known as "Sharkey" may be used (see Guo et al, (2010) *J. Mol. Biol.* doi:10.1016/j.jmb.2010.04.060).

Delivery

The nuclease described herein may be delivered to a target cell containing a TCR gene by any suitable means. Methods of delivering proteins comprising DNA-binding domains are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases as described herein may also be delivered using vectors containing sequences encoding one or more nucleases. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties.

In certain embodiments, the vector is a lentiviral vector. A lentiviral vector, as used herein, is a vector which comprises at least one component part derivable from a lentivirus. A detailed list of lentiviruses may be found in Coffin et at (1997) "*Retroviruses*" Cold Spring Harbour Laboratory Press Eds: J M Coffin, S M Hughes, H E Varmus pp 758-763). Lentiviral vectors can be produced generally by methods well known in the art. See, e.g., U.S. Pat. Nos. 5,994,136; 6,165,782; and 6,428,953. Preferably, the lentiviral vector is an integrase deficient lentiviral vector (IDLV). See, e.g., U.S. Patent Publication 2009/0117617. IDLVs may be produced as described, for example using lentivirus vectors that include one or more mutations in the native lentivirus integrase gene, for instance as disclosed in Leavitt et al. (1996) *J. Virol.* 70(2):721-728; Philippe et al. (2006) *Proc. Natl Acad. Sci USA* 103(47): 17684-17689; and WO 06/010834. In certain embodiments, the IDLV is an HIV lentiviral vector comprising a mutation at position 64 of the integrase protein (D64V), as described in Leavitt et al. (1996) *J. Virol.* 70(2):721-728.

In certain embodiments, the vector is an adenovirus vector. Non-limiting examples of Ad vectors that can be used in the present application include recombinant (such as E1-deleted), conditionally replication competent (such as oncolytic) and/or replication competent Ad vectors derived from human or non-human serotypes (e.g., Ad5, Ad11, Ad35, or porcine adenovirus-3); and/or chimeric Ad vectors (such as Ad5/F35) or tropism-altered Ad vectors with engineered fiber (e.g., knob or shaft) proteins (such as peptide insertions within the HI loop of the knob protein). Also useful are "gutless" Ad vectors, e.g., an Ad vector in which all adenovirus genes have been removed, to reduce immunogenicity and to increase the size of the DNA payload. This allows, for example, simultaneous delivery of sequences encoding ZFNs and a donor sequence. Such gutless vectors are especially useful when the donor sequences include large transgenes to be integrated via targeted integration.

Replication-deficient recombinant adenoviral vectors (Ad) can be produced at high titer, and they readily infect a number of different cell types. Most adenovirus vectors are engineered such that a transgene replaces the Ad E1a, E1b, and/or E3 genes; subsequently the replication defective vector is propagated in cells that provide one or more of the deleted gene functions in trans. For example, human 293 cells supply E1 function. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-1089 (1998)).

Additional examples of the use of adenovirus vectors for gene transfer in clinical trials include Rosenecker et al., *Infection* 24:1 5-10 (1996); Welsh et al., *Hum. Gene Ther.* 2:205-18 (1995); Alvarez et al., *Hum. Gene Ther.* 5:597-613 (1997); Topf et al., *Gene Ther.* 5:507-513 (1998).

In certain embodiments, the Ad vector is a chimeric adenovirus vector, containing sequences from two or more different adenovirus genomes. For example, the Ad vector can be an Ad5/F35 vector. Ad5/F35 is created by replacing one or more of the fiber protein genes (knob, shaft, tail, penton) of Ad5 with the corresponding fiber protein gene from a B group adenovirus such as, for example, Ad35. The Ad5/F35 vector and characteristics of this vector are described, for example, in Ni et al. (2005) "Evaluation of biodistribution and safety of adenovirus vectors containing group B fibers after intravenous injection into baboons," *Hum Gene Ther* 16:664-677; Nilsson et al. (2004) "Functionally distinct subpopulations of cord blood CD34+ cells are transduced by adenoviral vectors with serotype 5 or 35 tropism," *Mol Ther* 9:377-388; Nilsson et al. (2004) "Development of an adenoviral vector system with adenovirus serotype 35 tropism; efficient transient gene transfer into primary malignant hematopoietic cells," *J Gene Med* 6:631-641; Schroers et al. (2004) "Gene transfer into human T lymphocytes and natural killer cells by Ad5/F35 chimeric adenoviral vectors," *Exp Hematol* 32:536-546; Seshidhar et al. (2003) "Development of adenovirus serotype 35 as a gene transfer vector," *Virology* 311:384-393; Shayakhmetov et al. (2000) "Efficient gene transfer into human CD34(+) cells by a retargeted adenovirus vector," *J Virol* 74:2567-2583; and Soya et al. (2004), "A tumor-targeted and conditionally replicating oncolytic adenovirus vector expressing TRAIL for treatment of liver metastases," *Mol Ther* 9:496-509. As noted above, ZFNs and polynucleotides encoding these ZFNs may be delivered to any target cell. Generally, for inactivating a gene CCR-5, the cell is an immune cell, for example, a lymphocyte (B-cells, T-cells such as T helper ($T_H$) and T cytotoxic cells ($T_C$), null cells such as natural killer (NK) cells); a mononuclear cell (monocytes, marcophages); a granulocytic cell (granulocytes, neutrophils, eosinophils, basophils); a mast cell; and/or a dendritic cell (Langerhans cells, interstitial dendritic cells, interdigitating dendritic cells, circulating dendritic cells). Macrophages, B lymphocytes and dendritic cells are exemplary antigen-presenting cells involved in $T_H$ cell activation. In certain embodiments, the target cell is a $T_H$ cell, characterized by expression of CD4 on the surface. The target cell may also be a hematopoietic stem cell, which may give rise to any immune cell.

Applications

The disclosed methods and compositions can be used for inactivation of a TCR genomic sequence. As noted above, inactivation includes partial or complete repression of the endogenous TCR α and/or β gene expression in a cell. Inactivation of a TCR gene can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) or another coding sequence of interest into the gene or its regulatory region, so as to disrupt the gene or regulatory region, or by targeting recombination of a splice acceptor sequence into an intron to cause mis-splicing of the transcript. Inactivation of an endogenous TCR gene can also be accomplished by targeted recombination of a TCR gene(s) specific for a tumor antigen/MHC complex of interest.

There are a variety of applications for nuclease-mediated inactivation (knockout or knockdown) of a TCR gene. For example, the methods and compositions described herein allow for the generation and/or modification of cells lines (for therapeutic and non-therapeutic uses). Inactivation of the endogenous TCR gene(s) may be coupled with the insertion of genes encoding high avidity TCRs or chimeric antigen receptors (CARS, see Cartellieri et at (2010) *J Biomed and Biotech*, Vol 2010, Article ID 956304) against a known target, and the resultant transgenic cells (or descendants of these cells having the same characteristics) may be used as cellular therapeutics. Alternatively, the re-targeting of the T cell may occur in vivo, using viral vectors to deliver both the genes encoding the TCR-specific nucleases and the high avidity TCR on a donor nucleic acid. In either case, the materials and methods of the invention may be used in the treatment of cancer. Cells modified in vitro may also be used for modeling studies or for screening to find other types of therapeutics that may also work in concert with the TCR modification. Any type of cancer can be treated, including, but not limited to lung carcinomas, pancreatic cancers, liver cancers, bone cancers, breast cancers, colorectal cancers, ovarian cancers, leukemias, lymphomas, brain cancers and the like. Other diseases that may be treated with the technology of the invention include fungal, bacterial and viral infections as well as autoimmune diseases and graft-versus-host disease (GvHD).

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting.

EXAMPLES

Example 1: Expression of an Optimized, High Affinity WT-1 TCR Construct

Genes encoding for a codon-optimized, cysteine-modified TCR specific for an HLA-A2-restricted peptide from the Wilms tumor antigen 1 (WT1), specifically the WT1$_{126-134}$ peptide (Kuball et at (2007) *Blood* 109(6):2331-8) and single α21 or β21 WT1 specific TCR chains were cloned into bidirectional self-inactivating transfer vectors pCCLsin.PPT.ΔLNGFR.minCMV.WPGK.eGFP.Wpre or pCCLsin.cPPT.ΔLNGFR.min.CMV.hEF1a.eGFP.Wpre as described in Amendola et at (2005) *Nature Biotechnology* 23(1): 108-116, Thomas et at (2007) *J. Immunol* 179 (9): 5803-5810, and U.S. Patent Publication No US2006200869 (see FIG. 1A)

The vectors were packaged using an integrase-competent third generation lentivirus vector system, and pseudotyped by VZV envelope, essentially as described in Follenzi and Naldini (2002) *Methods in Enzymology* 346: 454-465. The lentiviral vectors were then used to transduce cells using standard techniques (see below) and cells were characterized by FACs analysis to determine if the exogenous TCRs were being expressed on the cell surface.

As shown below in Table 1, the WT-1 specific TCR construct was highly expressed, whether driven from the PGK/mCMV dual promoter combination or the EF1α/mCMV dual promoter construct. Numbers in Table are presented as percent of total signal present in the quadrant gated for VB21 expression and WT1-HLA-A2 pentamer binding.

TABLE 1

Expression of WT-1 TCR

| Promoter | Day 14 | Day 22 |
|---|---|---|
| PGK | 12.1 | 21.3 |
| EF1α | 1.48 | 5.16 |

Untransduced = 0.085

Figure 1B:
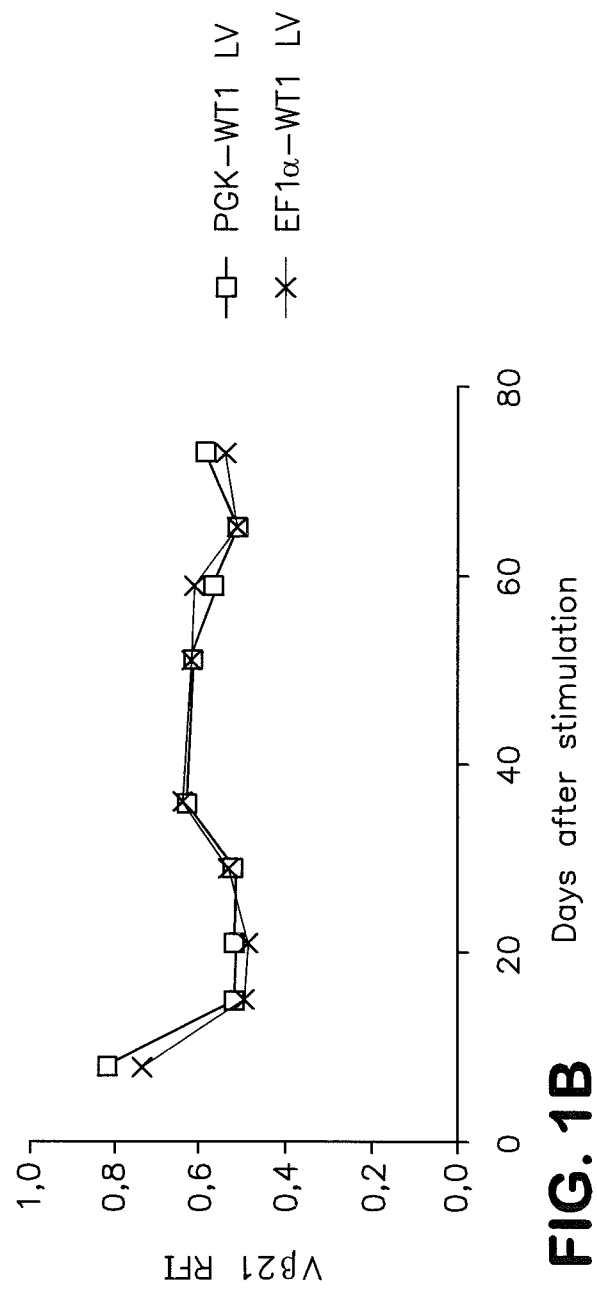

Transduction of T cells was accomplished by activating the cells with anti-CD3/anti-CD28 antibody-conjugated magnetic beads (Clin ExVivo CD3/CD28; Invitrogen) (baCD3/CD28) where the cells were cultured in IMDM (GIBCO-BRL), 10% FCS with low dose IL-7/IL-15 as described in European Patent Publication No EP1956080 and Koncko et at (2009) *Blood* 113: 1006-1015. This procedure preserved an early T cell differentiation phenotype (CD45RA−/+CD62L+, CD28+CD27+, IL7Ra+, IL-2+ γIFN−/+), and the cells proliferated indistinguishably from untransduced lymphocytes. In these conditions, the PGK dual promoter proved to be superior to the EF1α dual promoter in sustaining stochiometric expression of WT1-specific TCR chains, suggesting that the PGK bi-directional promoter exerts a higher activity in the antisense direction than the bi-directional EF1α promoter. Both promoters however, when tested in the context of a lentiviral vector, supported TCR expression at levels appropriate for efficient HLA-A2/WT1 pentamer binding (16%), for >70 days after initial stimulation (see FIG. 1B).

TCR transduced cells were also able to exhibit specific γIFN production and cytotoxic activity against WT1+HLA-A2+ primary leukemic blasts from AML patients. In particular, γIFN production in cells transduced with vectors expressing the transgenic TCRs either from the PGK/mCMV dual promoter combination or the EF1α/mCMV dual promoter was increased (FIG. 2A) as was % killing (lysis) by the TCR modified cells (FIGS. 2B and 2C). In addition, γIFN production was inhibited in the edited lymphocytes (FIG. 2D), in the presence of unlabelled targets expressing the HLA-restriction element and pulsed with the target peptide.

Example 2: Efficient Integration of a Transgene into the CCR5 Locus of Central Memory T Cells To test the idea of integrating the WT-1 specific TCR genes into a central memory T cell, GFP was used first as a donor nucleic acid to monitor transduction efficiency and GFP expression from the site of integration. The CCR5 locus was chosen because it has been shown that CCR5 knockout cells are fully functional (see U.S. Patent Publication No. 20080159996). In addition, the PPP1R12C (AAVS1) locus was similarly targeted (see US Patent Publication 20080299580) The GFP-encoding donor was transduced into the cell using an IDLV vector and the CCR5-specific ZFNs or AAVS1-specific ZFNs were introduced using a Ad5/F35 vector as described above. GFP expression was measured 20 days following transduction.

Figure 3A:
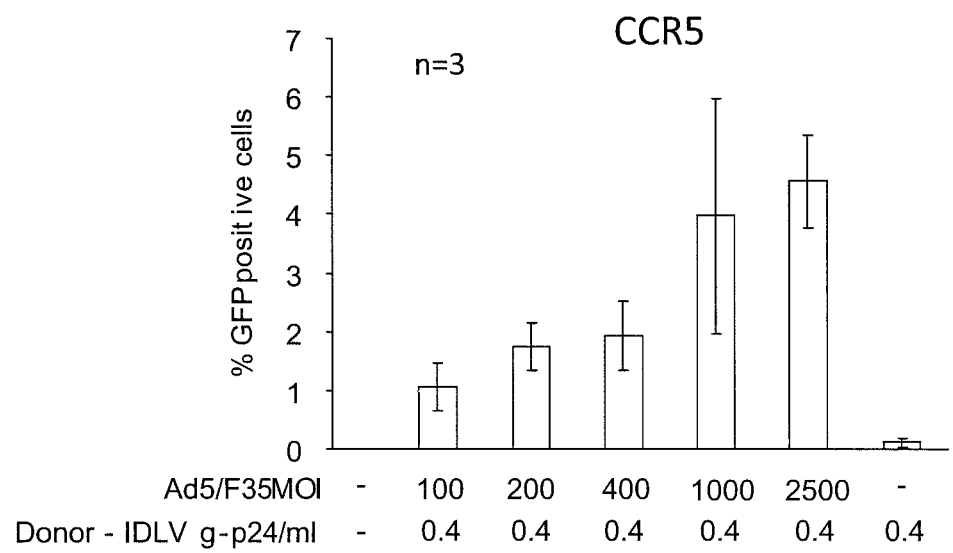
FIGS. 3A and 3B, are graphs depicting GFP expression following introduction of ZFNs targeted to a safe harbor locus together with a GFP donor.
Figure 3B:
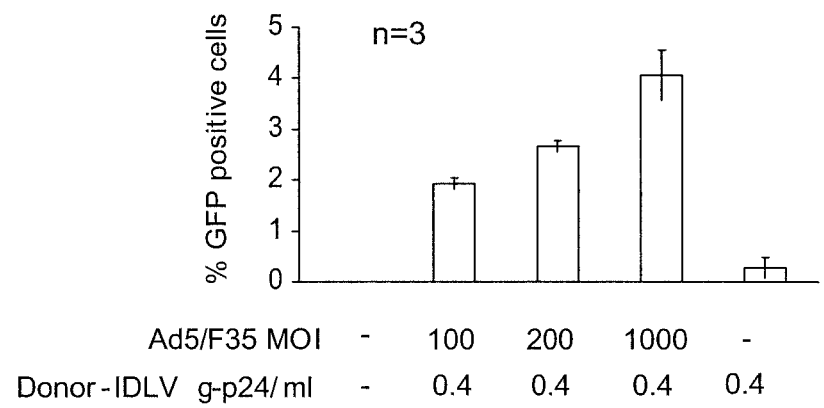

As shown in FIG. 3, ZFN-mediated integration of GFP transgenes resulted in increased GFP signals, including in relation to the amount of Ad5/F35 donor used (FIGS. 3A and 3B). Table 2 below shows the increase in the percent of GFP positive cells in the presence of donor or donor plus ZFNs.

TABLE 2

| GFP signal, percent positive cells | | | |
|---|---|---|---|
| Insert site | UT | +donor | donor + ZFN |
| CCR5 | 0.038 | 0.083 | 6.11 |
| AAVS1 | 0.015 | 0.18 | 4.38 |

Example 3: Integration of WT-1 Specific TCR Transgenes into the CCR5 Locus of Jurkat TCR β-Negative Cells The WT-1 specific TCR transgene construct was then used for targeted integration into the CCR5 locus of Jurkat cells that are TCR β-negative following treatment with TCR-β specific ZFNs. Cells were transfected using standard techniques with WT-1 TCR construct similar to that described in Example 1.

As seen in Table 4, after introduction of the WT-1 TCR donor (WT1-TCR IDLV) and the CCR5-specific ZFNs (Ad-ZFNs), there is a marked increase in Vβ21 staining or signal, while without the donor or the ZFNs, only background Vβ21 signal is seen. Thus, ZFN-mediated integration of the WT-1 specific TCR into the CCR5 locus occurred in a substantial percentage of the cells.

TABLE 4

| Percent of total signal from VB21 + expression | | | |
|---|---|---|---|
| WT1-TCR IDLV | + | + | + | − |
| Ad ZFNs | + | ++ | − | − |
| Percent VB21+ | 16.6 | 18.7 | 2.27 | 0.81 |

Example 4: Design of TCR-Specific ZFNs

TCR-specific ZFNs were constructed to enable site specific introduction of double strand breaks at either the TCRα and/or TCRβ genes. ZFNs were designed and incorporated into plasmids or IDLV vectors essentially as described in Urnov et al. (2005) *Nature* 435(7042):646-651, Lombardo et at (2007) *Nat Biotechnol*. November; 25(11):1298-306, and U.S. Patent Publication 2008/0131962. The recognition helices for exemplary ZFN pairs as well as the target sequence are shown below in Tables 5 and 6. Target sites of the TCR zinc-finger designs are shown in the first column. Nucleotides in the target site that are contacted by the ZFP recognition helices are indicated in uppercase letters; non-contacted nucleotides indicated in lowercase.

TABLE 5

TCR-α Zinc-finger Designs

| ZFN Name Target sequence | F1 | F2 | F3 | F4 | F5 | F6 |
|---|---|---|---|---|---|---|
| 25529 (ex 1) ctATGGA CtTCAAG AGCAaca gtgctgt (SEQ ID NO: 1) | QSGDL TR (SEQ ID NO: 2) | QRTHL KA (SEQ ID NO: 3) | QSGDR NK (SEQ ID NO: 4) | DRSNL SR (SEQ ID NO: 5) | RSDAL TQ (SEQ ID NO: 6) | N/A |
| 25528 (ex 1) ctCATGT CTAGcAC AGTTttg tctgtga (SEQ ID NO: 7) | TSGSL SR (SEQ ID NO: 8) | QSSVR NS (SEQ ID NO: 9) | RSDNL ST (SEQ ID NO: 10) | DRSAL AR (SEQ ID NO: 11) | LKQNL DA (SEQ ID NO: 12) | N/A |
| 25535 (ex 1) gtGCTGT GGCCtGG AGCAaca aatctga (SEQ ID NO: 13) | DRSAL SR (SEQ ID NO: 14) | QSGHL SR (SEQ ID NO: 15) | DRSDL SR (SEQ ID NO: 16) | RSDAL SR (SEQ ID NO: 17) | DRSDL SR (SEQ ID NO: 16) | N/A |
| 25534 (ex 1) ttGCTCT TGAAGTC cATAGAC ctcatgt (SEQ ID NO: 18) | DRSNL SR (SEQ ID NO: 5) | QKTSL QA (SEQ ID NO: 19) | DRSAL SR (SEQ ID NO: 14) | QSGNL AR (SEQ ID NO: 20) | GKEEL NE (SEQ ID NO: 21) | RSSDL SR (SEQ ID NO: 22) |
| 25537 (ex 1) gcTGTGG CCTGGAG CAAcaaa tctgact (SEQ ID NO: 23) | GNVDL IE (SEQ ID NO: 24) | RSSNL SR (SEQ ID NO: 25) | RSDAL SV (SEQ ID NO: 26) | DSSHR TR (SEQ ID NO: 27) | WRSCR SA (SEQ ID NO: 28) | N/A |
| 25536 (ex 1) ctGTTGC TcTTGAA GTCCata gacctca (SEQ ID NO: 29) | DSSDR KK (SEQ ID NO: 30) | RSDNL SV (SEQ ID NO: 31) | RRFIL RG (SEQ ID NO: 32) | QSGDL TR (SEQ ID NO: 2) | TSGSL TR (SEQ ID NO: 33) | N/A |
| 25538 (ex 1) ctGTGGC CtGGAGC AACAaat ctgactt (SEQ ID NO: 34) | QSGDL TR (SEQ ID NO: 2) | QTSTL SK (SEQ ID NO: 35) | QSGHL SR (SEQ ID NO: 15) | DRSDL SR (SEQ ID NO: 16) | RSDAL AR (SEQ ID NO: 36) | N/A |
| 25540 (ex 1) ctGACTT TGCATGT GCAaacg ccttcaa (SEQ ID NO: 37) | QSGDL TR (SEQ ID NO: 2) | WRSSL AS (SEQ ID NO: 38) | QSGDL TR (SEQ ID NO: 2) | HKWVL RQ (SEQ ID NO: 39) | DRSNL TR (SEQ ID NO: 40) | N/A |
| 25539 (ex 1) ttGTTGC TcCAGGC CACAGCA ctgttgc (SEQ ID NO: 41) | QSGDL TR (SEQ ID NO: 2) | QWGTR YR (SEQ ID NO: 42) | ERGTL AR (SEQ ID NO: 43) | RSDNL RE (SEQ ID NO: 44) | QSGDL TR (SEQ ID NO: 2) | TSGSL TR (SEQ ID NO: 33) |
| 22199 (ex 3) tgAAAGT GGCCGGG tttaatc tgctcat (SEQ ID NO: 45) | RSAHL SR (SEQ ID NO: 46) | DRSDL SR (SEQ ID NO: 16) | RSDHL SV (SEQ ID NO: 47) | QNNHR IT (SEQ ID NO: 48) | N/A | N/A |
| 22189 (ex 3) agGAGGA TTCGGAA cccaatc actgaca (SEQ ID NO: 49) | QRSNL VR (SEQ ID NO: 50) | RNDDR KK (SEQ ID NO: 51) | TSGNL TR (SEQ ID NO: 52) | TSANL SR (SEQ ID NO: 53) | N/A | N/A |
| 25572 (ex 3) gaGGAGG AtTCGGA ACCCaat cactgac (SEQ ID NO: 54) | DRSTL RQ (SEQ ID NO: 55) | QRSNL VR (SEQ ID NO: 50) | RNDDR KK (SEQ ID NO: 51) | RSAHL SR (SEQ ID NO: 46) | QSGHL SR (SEQ ID NO: 15) | N/A |
| 25573 (ex 3) gaGGAGG AtTCGGA Acccaat cactgac (SEQ ID NO: 54) | QRSNL VR (SEQ ID NO: 50) | RNDDR KK (SEQ ID NO: 51) | QSGHL AR (SEQ ID NO: 56) | QSGHL SR (SEQ ID NO: 15) | N/A | N/A |
| 22199 (ex 3) tgAAAGT GGCCGGG tttaatc tgctcat (SEQ ID NO: 57) | RSAHL SR (SEQ ID NO: 46) | DRSDL SR (SEQ ID NO: 16) | RSDHL SV (SEQ ID NO: 47) | QNNHR IT (SEQ ID NO: 48) | N/A | N/A |

TABLE 6

TCR-β Zinc-finger Designs

| ZFN Name Target sequence | F1 | F2 | F3 | F4 | F5 | F6 |
|---|---|---|---|---|---|---|
| 16783 ccGTAGA | RSDVLSA (SEQ ID | DRSNRIK (SEQ ID | RSDVLSE (SEQ ID | QSGNLAR (SEQ ID | QSGS LTR | N/A |

TABLE 6-continued

TCR-β Zinc-finger Designs

| ZFN Name Target sequence | F1 | F2 | F3 | F4 | F5 | F6 |
|---|---|---|---|---|---|---|
| ACTGGAC TTGacag cggaagt (SEQ ID NO: 58) | NO: 59) | NO: 60) | NO: 61) | NO: 20) | (SEQ ID NO: 62) | |
| 16787 tcTCGGA GAATGAC GAGTGGa cccagga (SEQ ID NO: 63) | RSDHLST (SEQ ID NO: 64) | RSDNLTR (SEQ ID NO: 65) | DRSNLSR (SEQ ID NO: 5) | TSSNRKT (SEQ ID NO: 66) | RSAN LAR (SEQ ID NO: 67) | RNDD RKK (SEQ ID NO: 51) |
| 22409 tcTCGGA GAATGAC GAGTGGa cccagga (SEQ ID NO: 63) | RSDHLST (SEQ ID NO: 64) | RSDNLTR (SEQ ID NO: 65) | DRSNLSR (SEQ ID NO: 5) | LQFNRNQ (SEQ ID NO: 68) | RSAN LAR (SEQ ID NO: 67) | RNDD RKK (SEQ ID NO: 51) |
| 22449 tcTCGGA GAATGAC GAGTGGa cccagga (SEQ ID NO: 63) | RSDHLST (SEQ ID NO: 64) | RSDNLTR (SEQ ID NO: 65) | DSSNLSR (SEQ ID NO: 69) | LRFNLSN (SEQ ID NO: 70) | RSAN LAR (SEQ ID NO: 67) | RNDD RKK (SEQ ID NO: 51) |
| 22454 tcTCGGA GAATGAC GAGTGGa cccagga (SEQ ID NO: 63) | RSDHLST (SEQ ID NO: 64) | RSDNLTR (SEQ ID NO: 65) | DSSNLSR (SEQ ID NO: 69) | LHFQLTG (SEQ ID NO: 71) | RSAN LAR (SEQ ID NO: 67) | RNDD RKK (SEQ ID NO: 51) |
| 25814 ccGTAGA ACTGGAC TTGacag cggaagt (SEQ ID NO: 58) | RSDVLSA (SEQ ID NO: 59) | DRSNRIK (SEQ ID NO: 60) | RSDVLSE (SEQ ID NO: 61) | QSGNLAR (SEQ ID NO: 20) | QSGS LTR (SEQ ID NO: 62) | N/A |
| 25818 ccGTAGA ACTGgaC TTGACag cggaagt (SEQ ID NO: 58) | DRSNLSR (SEQ ID NO: 5) | LKFALAN (SEQ ID NO: 72) | RSDVLSE (SEQ ID NO: 61) | QSGNLAR (SEQ ID NO: 20) | QSGS LTR (SEQ ID NO: 62) | N/A |
| 25820 ccGTAGA ACTGGAC TTGacag cggaagt (SEQ ID NO: 58) | RSDVLSA (SEQ ID NO: 59) | DRSNRIK (SEQ ID NO: 60) | RSDVLSE (SEQ ID NO: 61) | QSGNLAR (SEQ ID NO: 20) | QSGA LAR (SEQ ID NO: 73) | N/A |
| 25822 ccGTAGA ACTGGAC TTGacag cggaagt (SEQ ID NO: 58) | RLSVLTI (SEQ ID NO: 74) | DRANLTR (SEQ ID NO: 75) | RSDVLSE (SEQ ID NO: 61) | QSGNLAR (SEQ ID NO: 20) | QSGA LAR (SEQ ID NO: 73) | N/A |

Example 5: ZFN Activity In Vitro

The ZFNs described in Tables 5 and 6 were used to test nuclease activity in K562 cells. To test cleavage activity, plasmids encoding the pairs of human TCR-specific ZFNs described above were transfected into K562 cells. K562 cells were obtained from the American Type Culture Collection and grown as recommended in RPMI medium (Invitrogen) supplemented with 10% qualified fetal bovine serum (FBS, Cyclone). For transfection, one million K562 cells were mixed with 2 μg of the zinc-finger nuclease plasmid and 100 μL Amaxa Solution V. Cells were transfected in an Amaxa Nucleofector II™ using program T-16 and recovered into 1.4 mL warm RPMI medium+10% FBS.

Genomic DNA was harvested and a portion of the TCR locus encompassing the intended cleavage site was PCR amplified using the Accuprime HiFi polymerase from Invitrogen as follows: after an initial 3 minute denaturation at 94° C., 30 cycles of PCR were performed with a 30 second denaturation step at 94° C. followed by a 30 second annealing step at 58° C. followed by a 30 second extension step at 68° C. After the completion of 30 cycles, the reaction was incubated at 68° C. for 7 minutes, then at 4° C. indefinitely.

The genomic DNA from the K562 TCR-specific ZFN-treated cells was examined by the Cel-I assay as described, for example, in U.S. Patent Publication Nos. 20080015164; 20080131962 and 20080159996.

Figure 4A:
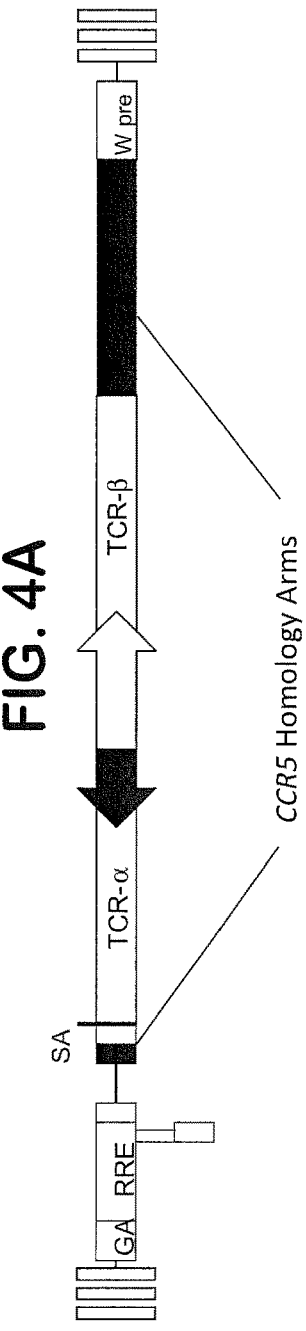
FIGS. 4A and 4B, depict diagrams of exemplary TCR-α and TCR-β donor molecules (FIG. 4A) and the TCR-β genes (FIG. 4B).
Figure 4B:

The TCR beta locus in K562 cells has two functional copies with high sequence similarity (TRBC1 and TRBC2) which are both targeted by TCR beta specific ZFNs. See, FIG. 4B. Thus, initially, PCR primers that would specifically amplify the regions around the intended ZFN cleavage sites specifically from either the TRBC1 or the TRBC2 genes were used to separately analyze NHEJ activity following ZFN driven cleavage for both genes. Results are presented in Table 7 below for ZFNs pair 16787 and 16783.

TABLE 7

NHEJ activity for pairs of TCR beta-specific ZFNs: analysis of TRBC1 and TRBC2

| NHEJ in TRBC2 | | | |
|---|---|---|---|
| TRBC2 | ZFN1 | ZFN2 | % NHEJ |
| | 16787 | 16783 | 8.68 |
| | | GFP | 0.00 |
| | | Mock | 0.00 |
| | | Water control | 0.00 |

| NHEJ in TRBC1 | | | |
|---|---|---|---|
| TRBC1 | ZFN1 | ZFN2 | % NHEJ |
| | 16787 | 16783 | 8.73 |
| | 21 | GFP | 0.00 |
| | 22 | Mock | 0.00 |
| | 23 | Water control | 0.00 |

The data presented in Table 7 demonstrate that the ZFNs cleave the TRBC1 and TRBC2 genes essentially equally.

In addition, we tested persistence of ZFN mediated modification of TRBC in K562 cells by harvesting samples at 3 and 10 days after transfection. Results are presented in Table 8 below and demonstrate that with the ZFN pair, 16787 and 16783, target gene modification is stable 10 days following transfection.

TABLE 8

TCR beta-specific ZFNs in K562 cells

| ZFN 1 | ZFN 2 | % NHEJ | |
|---|---|---|---|
| 22449 | 16783 | 20.1 | Day 3 |
| 22454 | 16783 | 17.7 | |
| 16787 | 16783 | 12.1 | |
| GFP | | 0.0 | |
| 22409 | 16783 | 14.7 | Day 10 |
| 22449 | 16783 | 8.1 | |
| 22454 | 16783 | 12.1 | |
| 16787 | 16783 | 15.6 | |
| GFP | | 0.0 | |

Figure 5:
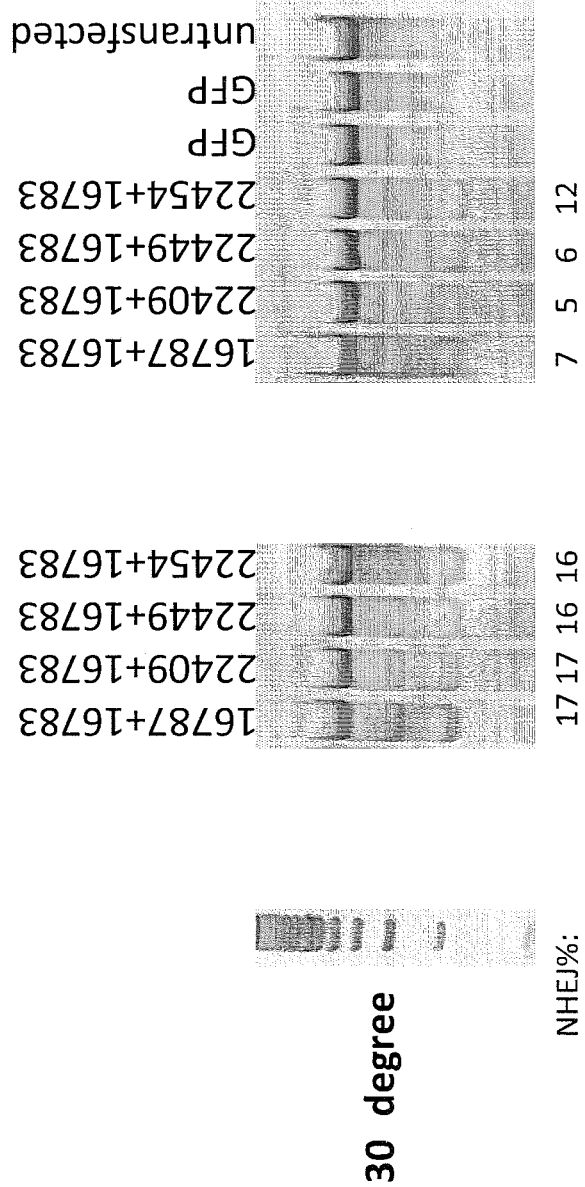
FIG. 5 depicts the percent modification for several pairs of TCR-β-specific ZFNs in K562 cells as measured by a Cel-I Surveyor™ mismatch assay ("Cel-I assay" Transgenomic) The cells were incubated initially at 30° C. following transfection, with either 0.1 or 0.4 μg of ZFN plasmid. Percent modification is shown at the bottom of the lanes.

Several ZFN pairs targeting TRBC were analyzed for NHEJ activity following varying amounts of input ZFN (either 0.4 or 0.1 μg of each ZFN). As shown in FIG. 5, all ZFN pairs tested exhibited high activity. In this experiment, the cells were treated with a 30° C. incubation period following transduction with the ZFNs (see U.S. patent application Ser. No. 12/800,599). Following analysis of TCR beta-specific ZFN cleavage in K562 cells, several ZFN pairs were tested in either CD4+ or CD8+ mature T cells. Briefly, CD8+ or CD4+ cells were purchased from AllCells and were cultured in RPMI+10% FBS+1% L-Glutamine (30 mg/mL)+IL-2 (30 μg/mL, Sigma) and allowed to rest for 4-24 hours.

Lentiviral vectors were constructed containing the ZFN pairs of interest. They were generated from the HIV derived self-inactivating vector construct and packaged using an HIV integrase carrying the D64V mutation and pseudotyped with the VSV-G envelope as described above. The Ad5/F35 adenoviral vectors were generated as described previously (Perez et al, (2008) *Nature Biotechnology* 26: 808-816) after cloning the two sets of ZFNs using a 2A sequence and a cytomegalovirus internal promoter. See, e.g., Holst J et at (2006) *Nat Protoc.* 1(1):406-17. 1e6 cells/nucleofection were used with the Amaxa™ Nucleofection kit as specified by the manufacturer for each transduction. Cells were activated 12-24 hours post nucleofection with anti-CD3/CD28 beads according to manufacturer's protocol (Invitrogen) and grown in IMDM (GIBCO-BRL), 10% FCS media supplemented with 5 ng/mL of IL-7 and IL-15 (Peprotech).

Cells were harvested 3 days after nucleofection and gene modification efficiency was determined using a Cel-I assay, performed as described in International Patent Publication WO 07/014275. See, also, Oleykowski et al. (1998) *Nucleic Acids Res.* 26:4597-4602; Qui et al. (2004) *BioTechniques* 36:702-707; Yeung et al. (2005) *BioTechniques* 38:749-758. Several of the ZFN pairs had good activity as measured by the Cel-I assay (NHEJ from 4-11.9%).

TCR-α-specific ZFNs were also tested in vitro as described above. The cells were incubated at 37° C. for 1 day following the transduction prior to shifting the incubation temperature to 30° C. as described above. See, U.S. Publication No. 20110129898. These ZFNs target the TRAC gene, results of a Cel-I assay performed on K562 cells that received various combinations of these ZFNs as described above showed high activity. See, FIG. 6.

Example 6: Disruption of TCR-β in Cells

The TCR-β-specific ZFNs were then used in experiments to specifically target the TCR locus. Initial experiments were designed to disrupt the TCR locus in Jurkat cells. TCR-β-specific ZFNS 16783 and 16787 were introduced on integrase-defective lentiviral vectors (IDLV) to transiently express the TRBC-targeting ZFNs. Transductions were performed with 0.25 μg or 0.5 μg doses of IDLV, based on measurements of HIV Gag p24 in the vector preparations, 48 hours after activation. Vector infectivity ranged from 1 to $5 \times 10^4$ transducing units/ng p24 by vector DNA titration on 293T cells. Cells were then assayed by FACS analysis for loss of the CD3 marker and CD3(−) cells were enriched using LD columns with anti-CD3 MACS Microbeads (Miltenyi Biotec) according to the manufacturer's instructions.

As shown below in Table 9, following transduction with the ZFNs, there was a vector dose-dependent abrogation of cell surface expression of the TCR/CD3 complex reaching up to 20% of treated cells.

TABLE 9

Loss of CD3 signal in Jurkat cells treated with TCR-β specific ZFN IDLVs

| | Untransformed | 0.25 μg IDLV | 0.5 μg IDLV |
|---|---|---|---|
| Percent CD3(−) | 2.7 | 13.4 | 20.2 |

Figures 7A, 7B:
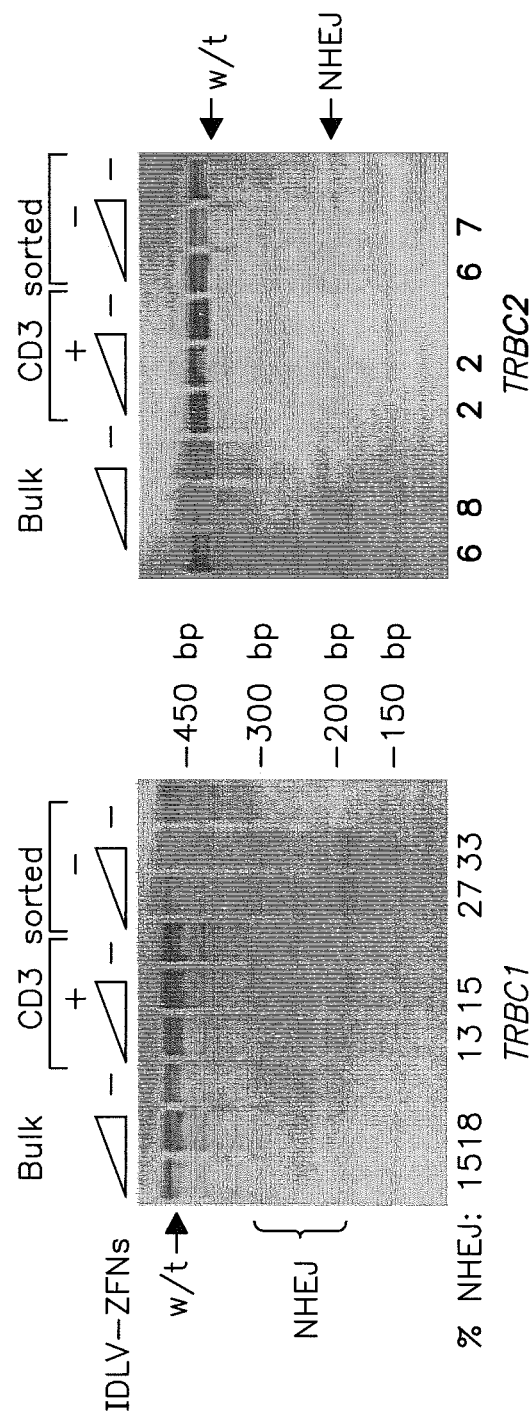

A Cel-I assay was performed and confirmed these results with up to 26% of the TRBC alleles (18% TRBC1 and 8% of TRBC2) disrupted in the ZFN treated cells (see FIGS. 7A and 7B, "Bulk").

Next, The TRBC ZFNs (16783 and 16787) were introduced into primary human T lymphocytes, and a similar level of CD3 disruption was observed by FACS, as seen in Jurkat cells. Peripheral blood T cells were harvested from healthy donors and activated with CD3 and CD28 conjugated beads. 48 hours post activation the cells were exposed to increasing doses of IDLVs containing the TRBC-specific ZFNs. The cells were then cultured in the presence of low dose (5 ng/mL) IL-7 and IL-15 to promote cell survival and growth. In the primary lymphocytes, up to 7% of the treated cells were CD3 negative while almost no CD3(−) cells were observed in the untreated control and the data is presented below in Table 10.

TABLE 10

Loss of CD3 signal in primary human T lymphocytes treated with TCR-β specific ZFN IDLVs

| | UT | 2.5 μg IDLV | 5 μg IDLV | 18.5 μg IDLV |
|---|---|---|---|---|
| Percent CD3 (−) | 0.17 | 2.94 | 3.26 | 7.07 |

Sorted CD3(−) lymphocytes could be expanded and survived over time in the presence of IL7 and IL15 (see FIGS. 7C and 7D), where percent modification is indicated in FIG. 7D. FIG. 7E further demonstrates that the CD3(−) cells persist in the population for at least 45 days and also show that the percent of CD3(−) cells in the population stays fairly constant over that time period. The CD3(−) cells do not appear to respond to non-specific mitogen stimulation since, PHA stimulation results in a decrease in the percent of CD3(−) cells in the pool due to expansion of the CD3(+) lymphocytes (FIG. 7F). This result demonstrates absence of CD3 functional signaling in the CD3(−) cells. No phenotypic differences were observed in the CD3(+) and CD3(−) lymphocytes which displayed a similar CD4/CD8 ratio. CD3(−) cells also maintain a central memory phenotype since they remain positive for CD62L, CD28 and IL-7RA (see Table 11 below).

TABLE 11

CD3(−) cells maintain a Central Memory Phenotype- percent of total fluorescence

|  | CD3(−) | CD3(+) |
|---|---|---|
| CD62L(+)/CD3(−) | 97.6 | 0 |
| CD62L(+)/CD3(+) | 1.25 | 98.4 |
| CD62L(−)/CD3(−) | 1.11 | 0 |
| CD62L(−)/CD3(+) | 0 | 1.61 |
| CD28(+)/CD27(−) | 4.66 | 3.23 |
| CD28(+)/CD27(+) | 93.4 | 94.7 |
| CD28(−)/CD27(−) | 0.87 | 0.68 |
| CD28(−)/CD27(+) | 0.97 | 1.43 |
| IL-7RA(+)/CD8(−) | 38.8 | 40.7 |
| IL-7RA(+)/CD8(+) | 47 | 47 |
| IL-7RA(−)/CD8(−) | 3.83 | 2.84 |
| IL-7RA(−)/CD8(+) | 10.4 | 9.42 |

Memory T lymphocytes are less dependent upon TCR signals for homeostatic proliferation than naive T cells; we thus investigated whether homeostatic cytokines could promote survival and growth of previously activated cells, in the absence of TCR expression. Remarkably, the TRBC-ZFNs treated cells could be expanded in culture by supplementation with low dose IL-7 and IL-15, with the proportion of CD3(−) cells remaining stable for more than 50 days in the absence of TCR triggering. Thus, ZFN exposure was well-tolerated in primary lymphocytes and resulted in the stable disruption of the targeted TRBC gene. Therefore, CD3(−) cells were sorted to near purity and further expanded with IL-7 and IL-15 for more than 3 weeks with growth rates similar to CD3(+) cells, demonstrating that homeostatic cytokines do not require TCR signaling functions to promote survival/proliferation of previously activated cells.

These data demonstrate the successful generation of a novel population of CD8 T cells with phenotypic characteristics of $T_{CM}$ but with surface expression of the endogenous TCR permanently disrupted.

Example 7: Introduction of aWT-1 Specific TCR in Cells that had Previously had the Endogenous TCR Permanently Disrupted CD3(−) T lymphocytes were sorted after treatment with the TCR β-specific ZFNs and a lentivirus used to randomly integrate the WT1-TCR β transgene as described in FIG. 1 (49.5±30% mean±SD transduction efficiency, n=4). Thus, in TCR-β-edited cells, expression of the transferred WT1-TCR from an integrated vector rescued surface translocation of CD3 (FIG. 8, 1$^{st}$ row).

Figure 8:
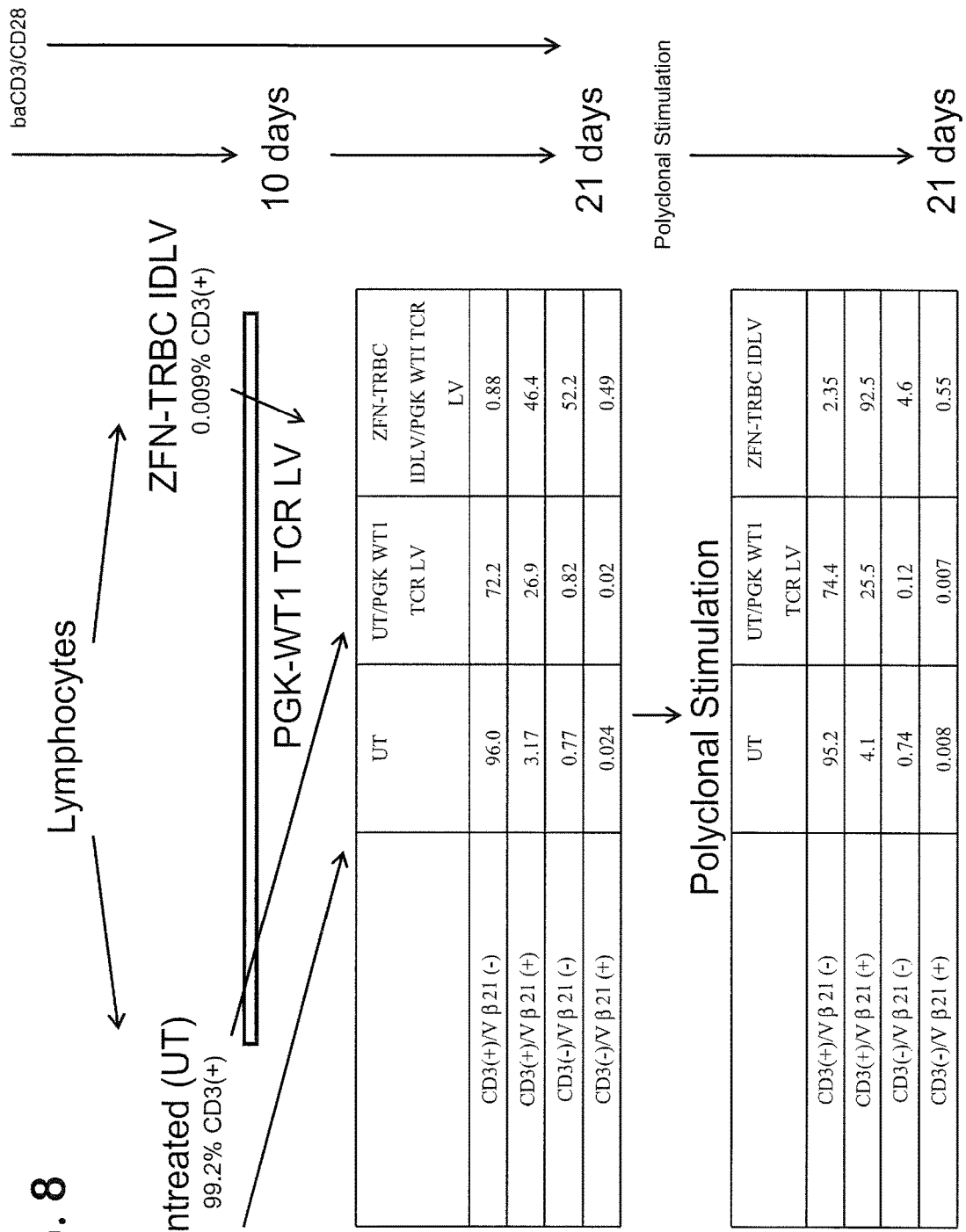
FIG. 8 depicts the experimental outline and the FACS results for editing of the TCR-β locus in primary T lymphocytes and the re-introduction of a specific TCR transgene. Cells used were either untreated primary T cells lymphocytes or lymphocytes pre-treated with the TCR-β-specific ZFNs carried by an IDLV and then sorted for CD3(−) primary T cells. Gene transfer was achieved after stimulation of T cells with cell-sized beads coated with antibodies directed to CD3 and to CD28, and cell culture in the presence of IL7 (5 ng/ml) and IL15 (5 ng/ml) to facilitate the generation of genetically modified central memory lymphocytes, according to European Patent Publication No EP1956080. As shown, cells that were sorted for being CD3(−) after treatment with the TCR-β specific ZFNs and then have the WT1-TCRβ V21.3 transgene randomly integrated into the genome using a lentiviral vector, show an increase in staining for both CD3 and for V21.3, indicating primary T lymphocytes can undergo endogenous TCR disruption via NHEJ using the TCR-β-specific ZFNs and then be re-targeted to recognize a specific antigen via the introduction of a new TCR encoded by a transgene cassette (PGK-WT1). As a control, UT cells also had the PGK-WT1 cassette inserted and showed a smaller percentage of cells expressing Vβ 21.3 (26%) as compared to the ZFN-treated, CD3(−) population (46%, 92% after polyclonal stimulation), indicating the disruption of the endogenous TCR may improve the cell-surface expression and functionality of the TCR expressed from the transgene.

In contrast to unedited TCR-transferred lymphocytes in which there was no inherent growth advantage to expression of the introduced TCR (FIG. 8, 2$^{nd}$ row) with respect to the untransduced cells on polyclonal expansion, TCR β chain disrupted cells containing the WT1-TCR could be enriched to >90% purity by polyclonal stimulation, indicating that surface expression of the transferred TCR/CD3 complex in TCR-β-edited cells was necessary and sufficient to promote TCR-mediated expansion of genetically modified cells (FIG. 8, 1$^{st}$ row). The exogenous WT1-TCR Vβ chain (Vβ21) was expressed in TCR-β chain disrupted lymphocytes at approximately 2-fold higher mean levels than in unedited TCR-transferred cells and reached expression levels similar to those of the endogenous Vβ21 chain of control T cells and was stably maintained in culture (FIG. 9A and FIG. 9B). Accordingly, after transduction with the same dose of PGK-WT1 LV, up to 22% of TCR-β-edited lymphocytes bound the WT1$_{126-134}$ pentamer as compared to only 2.6% of unedited cells. (FIG. 9A, lower histogram).

Thus, in the absence of competition from the endogenous TCR β chain, surface expression of the transgenic TCR β chain reaches physiological levels. To verify the function and avidity of TCR-β-edited lymphocytes, we compared TCR β chain disrupted cells with unedited cells transduced with the same PGK-WT1 LV for the ability to lyse HLA-A2$^+$ targets pulsed with increasing WT1$_{126-434}$ peptide concentrations (see FIG. 9C). This functional assay measures activity by a $^{51}$Chromium release assay for lysis of labeled T2 cells pulsed with increasing concentrations of the WT1$_{126-134}$HLA-A2 restricted peptide, or with the irrelevant CMV-derived pp65$_{494-503}$ HLA-A2 restricted peptide (10 μM, Proimmune) as a negative control, at an Effector/Target (E/T) ratio of 12.

Edited T cells were stimulated and 3 weeks later were tested for recognition of the labeled T2 cells by co-incubation for 5 hours. TCR β chain disrupted cells (denoted TCR-edited in FIG. 9C) killed targets more effectively than unedited (denoted TCR-transferred) WT1 LV transduced cells (EC50: edited cells: 90.51 nM, with 95% CI: 48.84-167.7; unedited TCR-transferred cells: 269.1 nM, with 95% CI: 175.1-413.5), likely reflecting the higher frequency and expression level of the transgenic WT1 TCR in the TCR-β edited samples. EC50 was calculated by non-linear regression analysis of $^{51}$Chromium release data by using the sigmoidal dose-response equation of the GraphPad Prism Software.

Results are represented as average SD of % lysis (*=p<0.05, **=p<0.01, TCR-edited n=6, TCR transferred, n=4). To assess reactivity at a single cell level, cell were analyzed for Vβ21 expression (see Table 12 below) which showed that, despite fairly equal copy number of the vectors, Vβ21 expression was greater in the TCR-edited cells.

TABLE 12

TCR expression and vector copy number/cell in TCR transferred and TCR edited lymphocytes

|  | Disruption endogenous β chain by TRBC-ZFN | PGK-WT1 LV or EF1α-WT1 LV | Vβ21 RFI* | % Vβ21+ cells | CpC$^§$ |
|---|---|---|---|---|---|
| TCR-transferred | No | EF1α-WT1 LV | 0.41 | 36.7 | 1.9 |
|  |  | PGK-WT1 LV | 0.54 | 62.7 | 2.1 |
| TCR-edited | Yes | PGK-WT1 LV | 0.91 | 97.3 | 1.2 |
| UT | No | None | 1 | 3.2 | 0 |

*TCR expression was measured by flow cytometry and was plotted as relative fluorescence intensity (RFI = Vβ21 MFI of transduced cells/Vβ MFI of untransduced cells).
$^§$Vector copy per cell (CpC) was measured by quantitative PCR as described (Kessels et al, (2001) *Nature Immunol* 2 (10): 957-61).

Figures 10A, 10B:
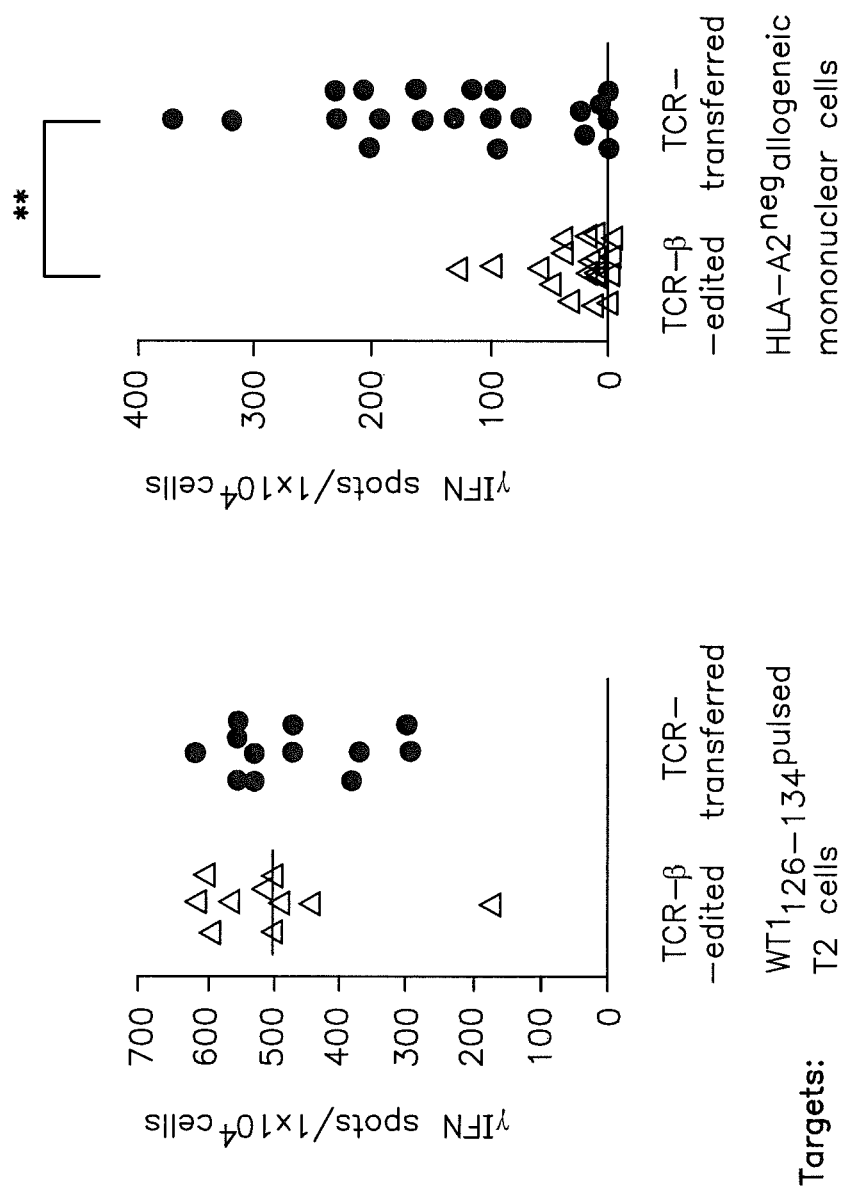
FIGS. 10A and 10B, depict the functional activity of WT1 TCR-positive T cell clones as tested by γIFN ELISpot assay. Clones were exposed to T2 cells pulsed with 10 nM of the $WT1_{126-134}$ HLA-A2 restricted peptide (10A), or to allogeneic PBMC (10B) at a stimulator/responder ratio of 1:1. The number of specific spots (open triangles and dark circles) observed is shown on the y axis as number of spots produced in presence of stimulators minus the number of spots produced by effectors alone. The results show that the TCR-β edited clones exhibit a higher degree of HLA A haplotype specificity than the TCR transferred cells which contain both the endogenous and the exogenous TCR genes.

To assess alloreactivity at a single cell level, clones were isolated and expanded from both TCR-β edited and TCR-transferred cells, previously sorted for WT1$_{126-134}$ pentamer binding to enrich for cells displaying optimal exogenous TCR expression. Clones were exposed to T2 cells pulsed with 10 nM of the WT1$_{125-134}$ HLA-A2 restricted peptide (left panel) or to allogenic PRMC (right panel) at a stimulator/responder ratio of 1. The number of specific spots is shown on the y axis as the number of spots produced in the presence of stimulators minus the number of spots produced by effectors alone (**=p<0.01). TCR β-edited clones displayed reduced alloreactivity, compared to TCR-transferred cells (see FIG. 10, compare the 10A to 10B), possibly reflecting the reduced risk of TCR mispairing in the absence of one endogenous TCR chain.

These data demonstrate the functional advantage offered by expression of a tumor specific exogenous TCR in a host CTL with abrogated endogenous TCR-β chain expression.

Figure 11:
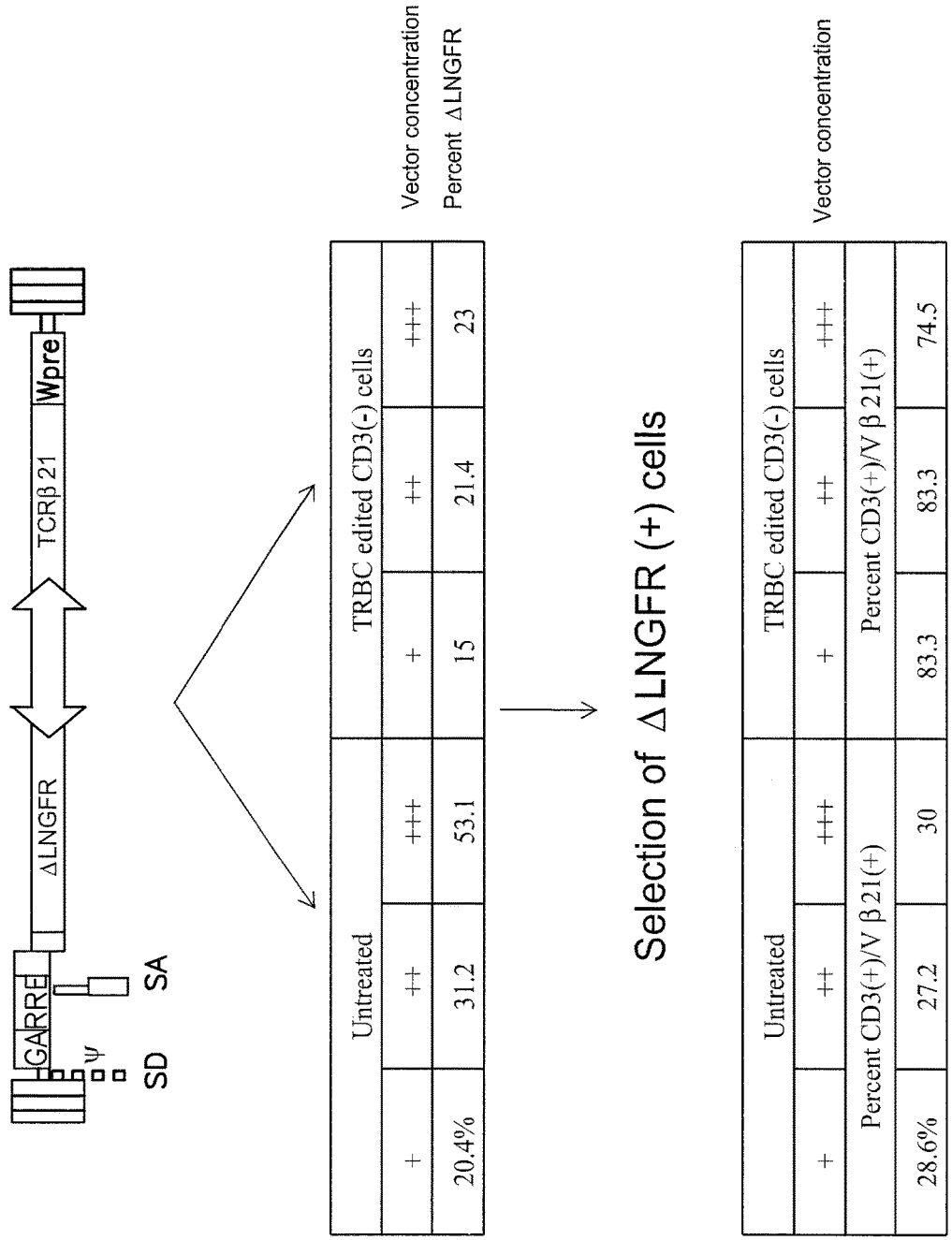
FIG. 11 depicts Vβ21 expression in ZFN-edited and unedited cells. CD3(−) cells sorted from TRBC-disrupted lymphocytes and unedited cells and were transduced at increasing MOI by LV encoding the Vβ21 gene of the WT1-specific TCR and the ΔLNGFR gene (see diagram at the top of figure showing dual expression of the Vβ21 gene and the ΔLNGFR gene). Transduction efficiency was assessed as % of $ΔLNGFR^{pos}$ lymphocytes and is shown. Vβ21 expression was measured on $ΔLNGFR^{pos}$ cells and demonstrates that the transduced Vβ21 gene can be expressed and form active CD3 complexes with the endogenous TRAC genes. The mean fluorescence intensity (MFI) of Vβ21 is shown.

Theoretically, surface re-expression of the unedited endogenous TCR α chain may still occur in TCR-β edited cells, following TCR gene transfer. To directly assess the potential for mispairing in TCR-β chain disrupted lymphocytes, CD3(−) cells were transduced with a LV encoding only the WT1-specific TCR β chain gene and the ΔLNGFR marker (WT1-β-ΔLNGFR-LV). Transduction efficiency was assessed as a percentage of the ΔLNGFR$^{pos}$ lymphocytes (see FIG. 11). Vβ21 expression was measured on ΔLNGFR$^{pos}$ cells. The mean fluorescent intensity (MFI) of Vβ21 is indicated. Despite the absence of WT1-specific α chain, Vβ21 expression was detected in up to 83% of ΔLNGFR$^{pos}$ TRBC-disrupted cells, demonstrating that even a cysteine-modified TCR β chain inserted into a cell with a TRBC disruption is capable of mispairing with the endogenous TCR α chain.

Next, CD3(−) lymphocytes are used to introduce the WT1-TCR β donor construct into the endogenous TCR locus. The donor is constructed as described above and used in conjunction with the TCR-β-specific ZFNs to cause integration of the TCR-β transgene at the endogenous locus. The cells become positive for both CD3 and the VB 21.3 TCR β chain.

Example 8: Disruption and Targeted Integration of the TCR-α Chain

Figure 12A:
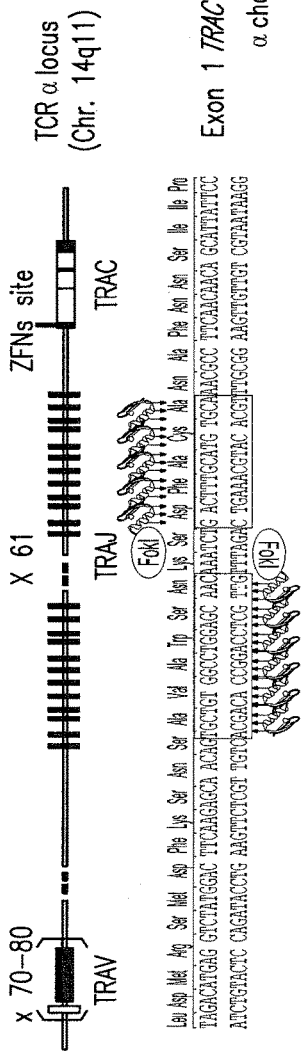
FIGS. 12A through 12C, depict CD3 expression in primary lymphocytes treated with ZFN targeting TCR α genes.
Figure 12B:
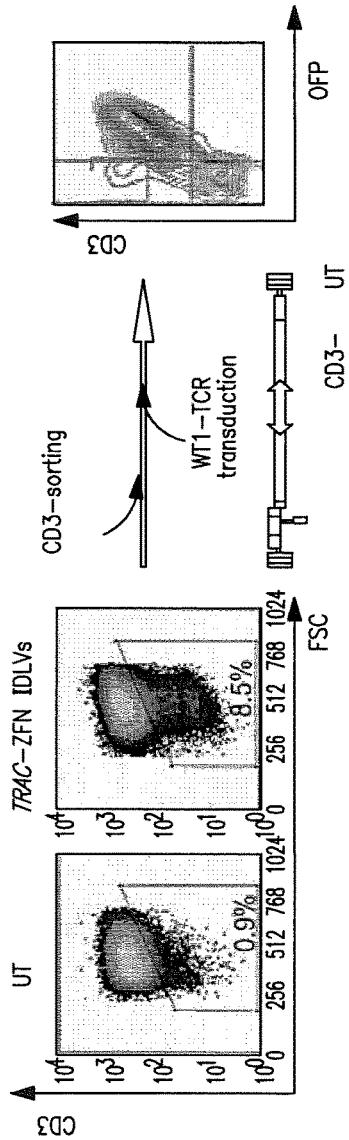
Figure 12C:
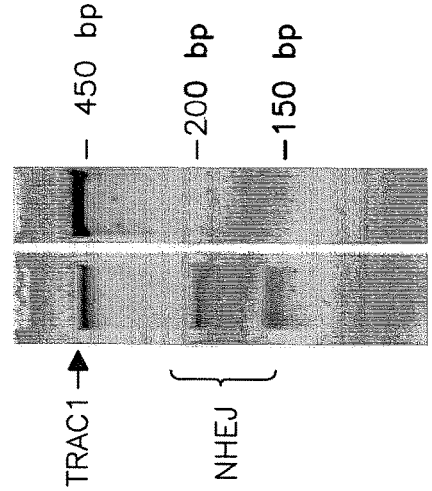
Figure 13:
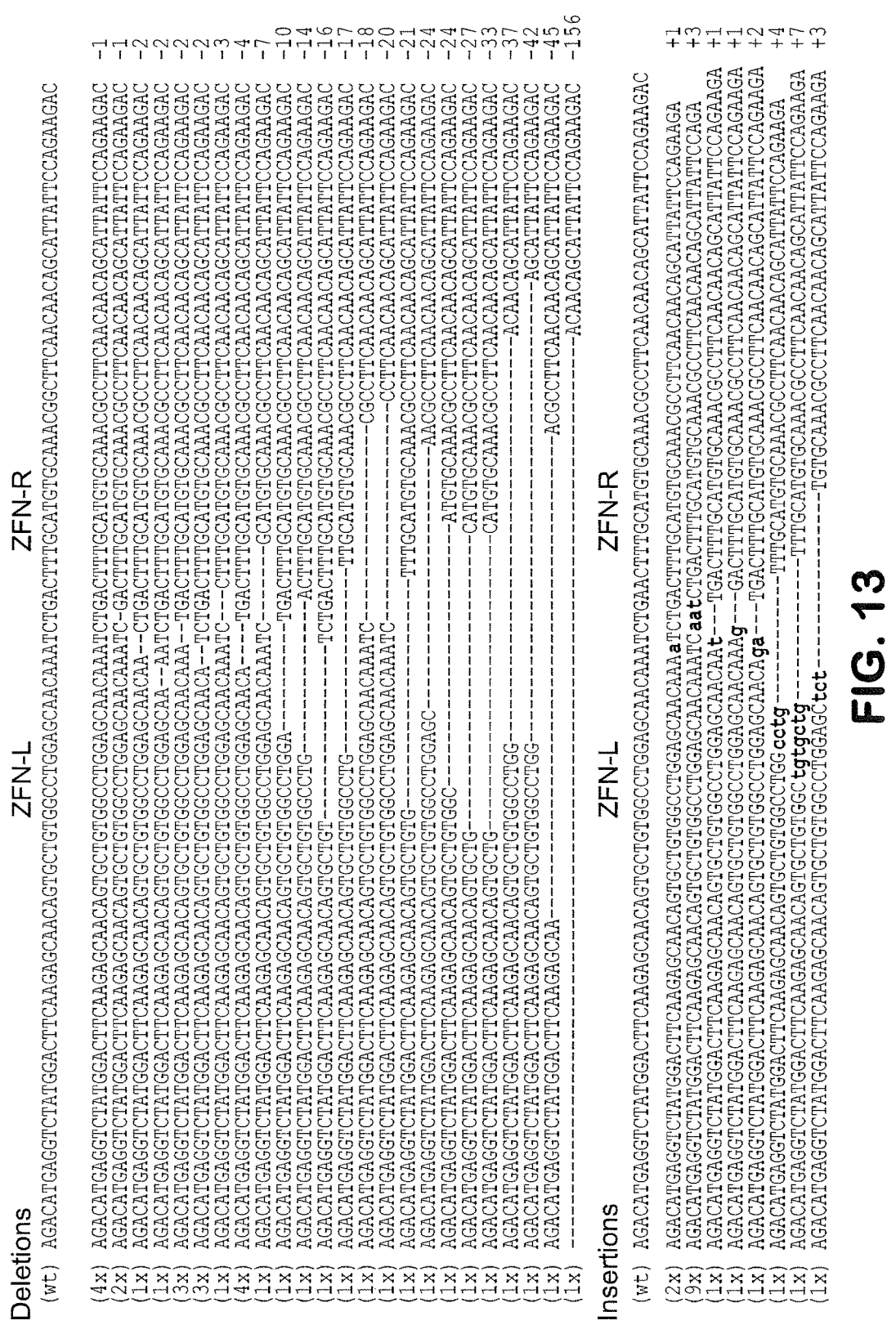

To eliminate the potential for TCR chain mispairing, we designed a pair of ZFNs targeting the constant region of the TCR α chain (TRAC) gene (FIG. 6) and obtained TCR-α-edited T lymphocytes (see FIG. 12A), following the same protocol described to TCR-β editing) and obtained TCR-α-edited T lymphocytes, following the same protocol described for TCR-β-editing (FIG. 12B, 12C, 13). To design a complete α/β TCR editing protocol that permits rapid isolation of engineered cells at each step of chain disruption/replacement, we generated a set of LV carrying a single α or β WT1-specific TCR chain, and used IDLV or adenoviral vectors (AdV) to transiently express TRBC- or TRAC-targeting ZFNs in lymphocytes (FIG. 14 for timeline and representative flow conditions/results for full TCR editing)

CD3(−) cells were efficiently generated with every ZFN-containing vector tested and sequencing at the site of nuclease cleavage reveals the small insertions and deletions (indels) present after repair by NHEJ (FIG. 13). AdVs, which proved more efficient in mediating TCR gene disruption than IDLVs, were selected for the purpose of complete TCR editing. T cells harvested from healthy donors were first exposed to TRAC-ZFN-Ad5/F35 48 hrs post-activation with baCD3/CD28, cultured in the presence of IL-7 and IL-15, and the resulting CD3(−) cells isolated by sorting were transduced (49±29& mean±SD transduction frequency, n=3) with a LV encoding the WT1-α chain (WT1-α LV).

Figure 14:
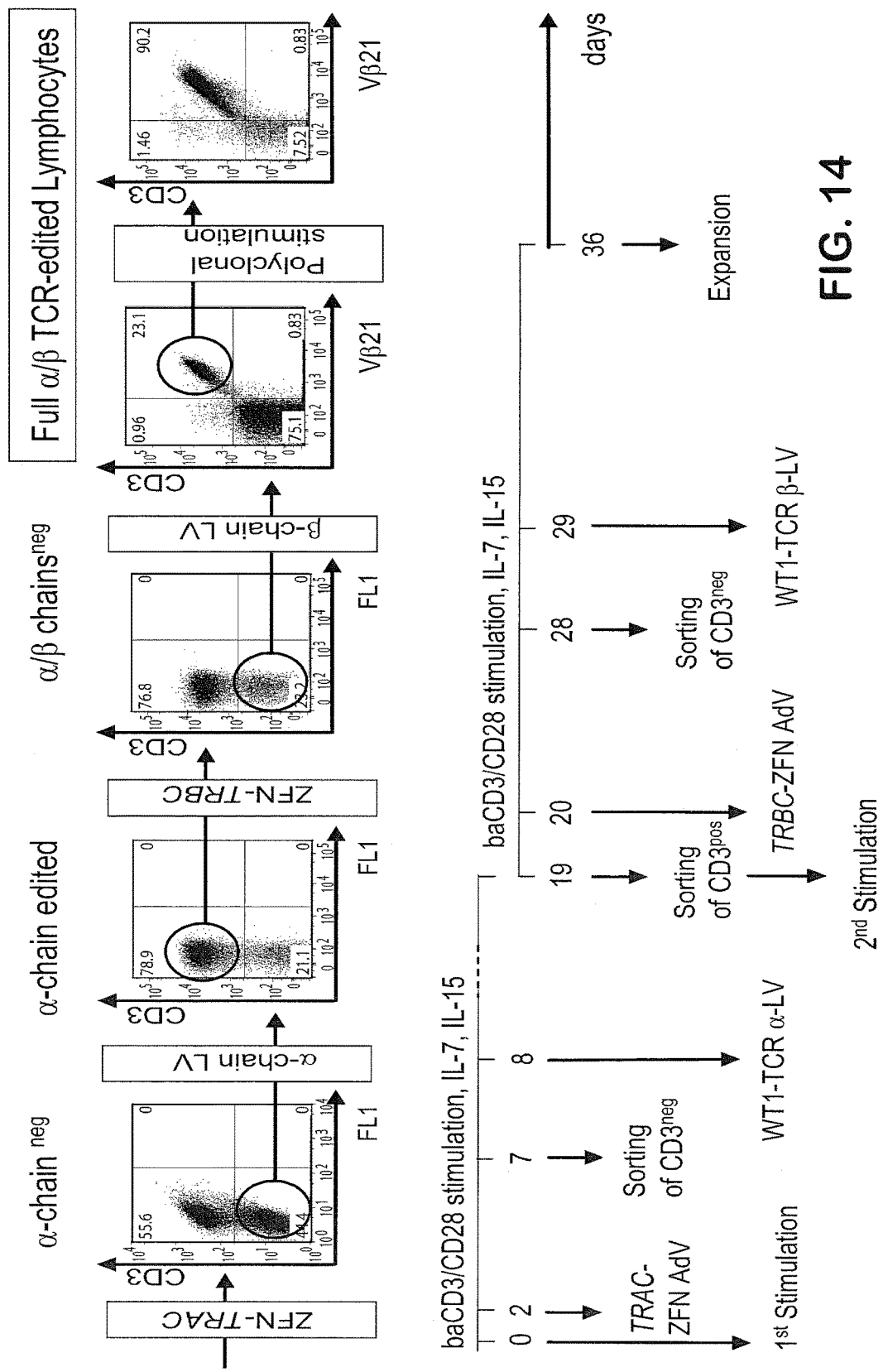
FIG. 14 depicts expression of CD3 in following ZFN editing. Upper panels shows results of studies in which activated T lymphocytes were treated with TRAC-ZFN-AdV (MOI 1000), and CD3(−) lymphocytes were sorted and transduced with 3 μg-p24/$10^6$ cells of PGK-WT1-α LV and CD3(+) cells were sorted. Surface expression of CD3 in transduced cells is shown. After one cycle of polyclonal stimulation, α-edited lymphocytes were treated with TRBC-ZFN-AdV (MOI $10^4$) and CD3(−) cells sorted and transduced with 3 μg-p24/$10^6$ cells of PGK-WT1-13 LV. Surface expression of Vβ21 TCR and CD3 is shown on transduced cells before and after one cycle of polyclonal stimulation. Percent of events measured in each quadrant are shown, and the experimental timeline is shown on the bottom. Timeline is shown on the bottom.
Figure 15:
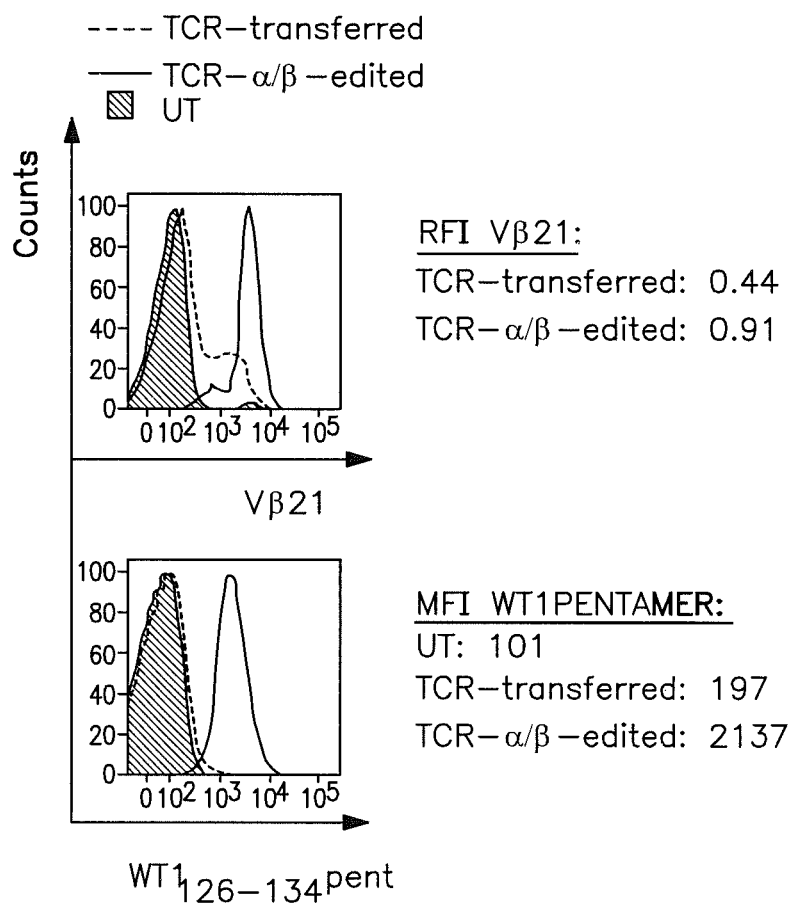
FIG. 15 depicts Vβ21 TCR expression (upper histogram) and $WT1_{126-134}$ pentamer binding (lower histogram) are shown in CD8(+) T cells with TCR α/β chains disrupted via introduction of ZFNs and sorting for CD3− cells followed by transduction with the WT1 TCR chains and sorting for CD3+ cells (TCR-edited), unedited WT1 LV transduced cells (TCR-transferred), and untransduced lymphocytes treated with the same culture conditions. The data show that the TCR edited cells have a higher level of Vβ21 expression than those clones wherein both the endogenous and the exogenous TCR genes are present. It also demonstrates that the TCR edited cells display higher binding to the WT1 peptide than those cells that have both sets of TCR genes.

Cells with rescued CD3 expression were then sorted, stimulated with baCD3/CD28 for one cycle, and then exposed to TRBC-ZFN-Ad5/F35. The second round of ZFN exposure yielded up to 23±4% newly CD3(−) cells, indicating that primary T lymphocytes are permissive to multiple rounds of ZFN manipulation. The CD3(−) cells were sorted and transduced (18±7% mean±SD transduction efficiency, n=3) with a WT1 TCR-β chain LV. Expression of the transferred WT1-β chain again rescued surface translocation of CD3, which was now co-expressed in balanced proportion with the WT1-TCR Vβ chain in TCR-edited cells (FIG. 14 and FIG. 15). In contrast to unedited TCR-transferred lymphocytes, TCR-α/β disrupted cells could be enriched to near purity by polyclonal stimulation following TCR gene transfer, and homogenously expressed the high levels of WT1-specific TCR required to bind the WT1$_{126-434}$ pentamer (see FIG. 15).

These results indicate that surface expression of the transferred TCR/CD3 complex in TCR-edited cells was necessary and sufficient to promote expansion of the cells with the desired specificity for WT1 (FIG. 14, right plot). Disruption of the α and β TCR chains was confirmed in TCR-α/β edited cells by Cel-I analysis. No phenotypic differences were observed in TCR-transferred and TCR α/β-edited lymphocytes, which displayed a $T_{CM}$ surface phenotype, as evidenced by high expression of CD62L, CD27, CD28 and IL-7rα. To verify the function and allogenic response of the fully edited lymphocytes, TCR α/β-edited and TCR transferred lymphocytes were polyclonally stimulated.

Figure 16A:
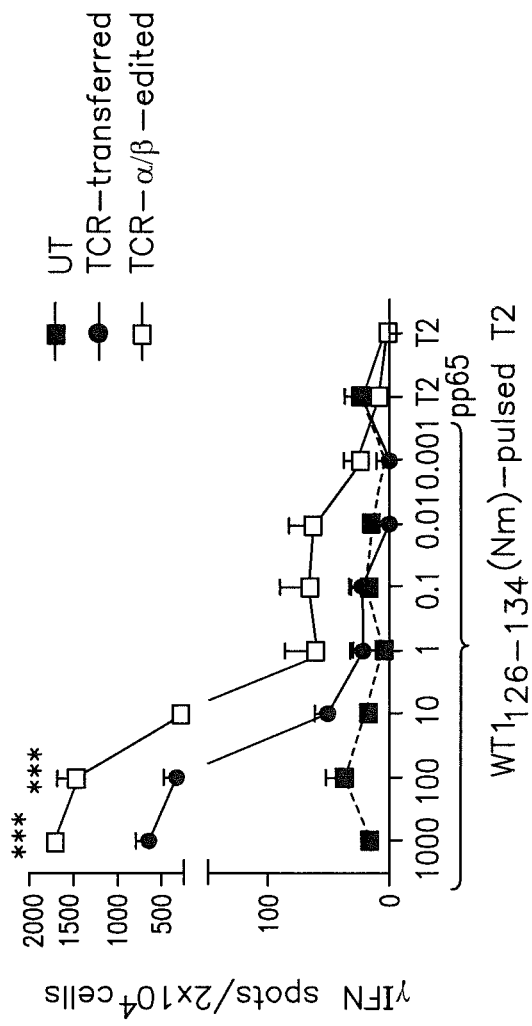
FIGS. 16A through 16C, are graphs depicting functional activity of genetically modified lymphocytes was tested by the γIFN ELISpot assay. Three weeks after polyclonal stimulation, TCR-α/β-edited and TCR transferred lymphocytes were exposed to either i) T2 cells pulsed with increasing concentrations of the $WT1_{126-134}$ HLA-A2 restricted peptide, or with the irrelevant CMV-derived $pp65_{495-503}$ HLA-A2 peptide (see FIG. 16A, right side of figure) or ii) $WT1^+$ HLA-A2(+) (black in FIG. 16B) or HLA-A2(−) (grey) leukemic cells harvested from AML patients with (dashed symbols) or without (full symbols) pulsing with $WT1_{126-134}$ peptide (50 nM).
Figure 16B:
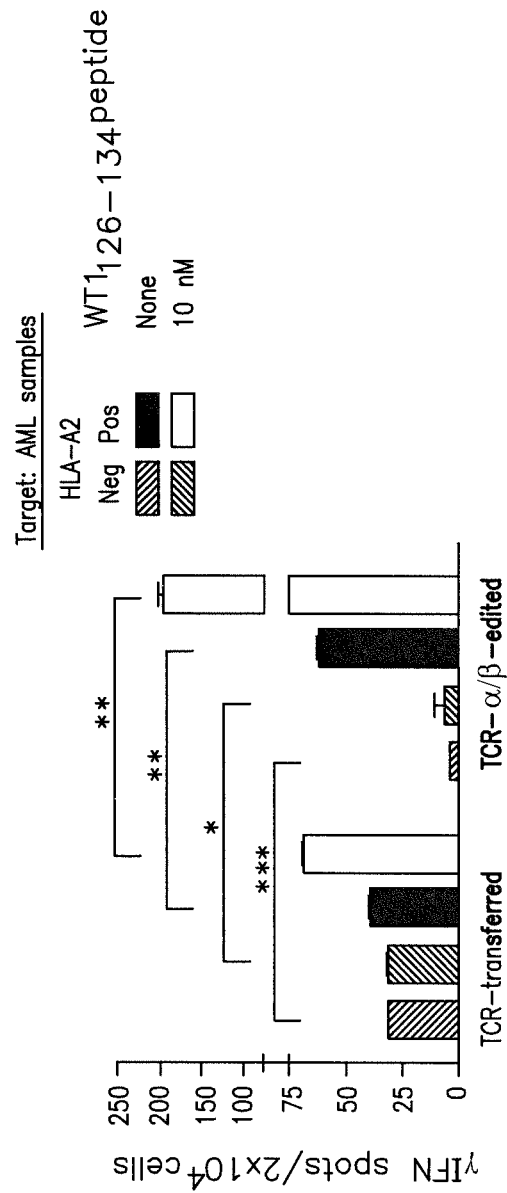
Figure 16C:
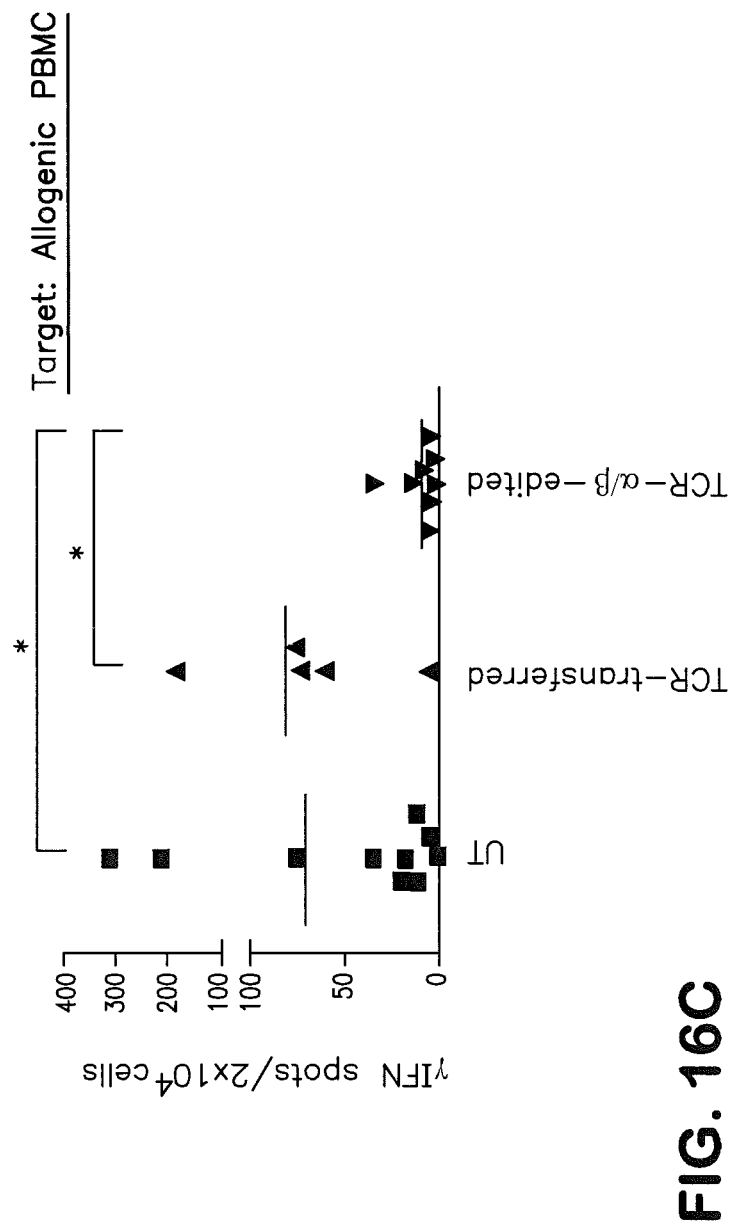

Three weeks after polyclonal stimulation, TCR-α/β-edited and TCR transferred lymphocytes were exposed to either i) T2 cells pulsed with increasing concentrations of the WT1$_{126-134}$ HLA-A2 restricted peptide, or with the irrelevant CMV-derived pp65$_{495-503}$ HLA-A2 peptide (see FIG. 16A) or ii) WT1$^+$ HLA-A2$^+$ (black in FIG. 16B) or HLA-A2$^-$ (grey) leukemic cells harvested from AML patients with (dashed symbols) or without (full symbols) pulsing with WT1$_{126-134}$ peptide (50 nM). FIG. 16C shows similar results where allogenic PBMC were used as target. All assays were performed at a stimulator/responder ratio of 1. Specific spots are shown on the y axis as spots produced in presence of stimulators minus spots produced by effectors alone. *=p<0.05, =p<0.01, *=p<0.001.

Example 9: Potential Off Target Cleavage Analysis

In silico analysis was used to identify the most likely potential off-target cleavage sites for both the TRAC- and TRBC-specific ZFN pairs as described in Perez et at (ibid). Sites were identified that contained up to 10 recognition site mismatches for either heterodimer ZFN pairs or homodimer pairs, although the most likely potential off target sites for these ZFN pairs were all targets for ZFN homodimers. The most likely potential off target sites identified are shown below in Tables 13 (TRAC) and 14 (TRBC).

TABLE 13

| Potential off target sites for TRAC-specific ZFNs | | | | | |
|---|---|---|---|---|---|
| Label | Chromo-some | Start site | Sequence | # mismatches | Gene |
| OT1 | 20 | 20683361 | AGGCACAaGCAAtGTCACA AGtACcaTGCtTGTACTT (SEQ ID NO: 76) | 6 | RALGAP A2 |

TABLE 13-continued

Potential off target sites for TRAC-specific ZFNs

| Label | Chromo-some | Start site | Sequence | # mismatches | Gene |
|---|---|---|---|---|---|
| OT2 | 6 | 10525974 | AGGTACAaGtAAAGaCGTAT GaACTTTGCtTGTACTT (SEQ ID NO: 77) | 5 | GCNT2 |
| OT3 | X | 135000000 | AAaTACAaGCcAAGcCAAGG TGgCTTTGCGTGTAaAT (SEQ ID NO: 78) | 6 | — |
| OT4 | 18 | 60239118 | ATaTACAattAAAGTCAGCTT TtACTTTGCagtTACTT (SEQ ID NO: 79) | 8 | ZCCHC2 |
| OT5 | 7 | 48500931 | TAGaACAtcCAAAcTCTGGA CCGACTTTGCaTGTcCAG (SEQ ID NO: 80) | 6 | ABCA13 |
| OT6 | 7 | 141000000 | ATtCAaACaCAAAGTCCCGT GGAtTTTGCtTtTAaAT (SEQ ID NO: 81) | 7 | — |
| OT7 | 8 | 2463159 | ATGCAggaGCAAgGTCACTC TGACcTTcCtTtgcCTT (SEQ ID NO: 82) | 10 | — |
| OT8 | 18 | 4312947 | ATGCACACaCAAAcTCATTT AagCTTTGCtTtTcCAT (SEQ ID NO: 83) | 7 | — |
| OT9 | 11 | 70854569 | CAGCcCAtGgAAtGTCATTCT cACaTTGCtTGTGCTT (SEQ ID NO: 84) | 7 | SHANK2 |
| OT10 | 13 | 57970961 | AAGCAaAaGaAAAaTCAATA TGACTTgGCtTtgGCTT (SEQ ID NO: 85) | 8 | — |
| OT11 | 2 | 69188623 | AAGgtCACtCActGTCTGTGT GGAgTTTGCGTGTcCTC (SEQ ID NO: 86) | 7 | — |
| OT12 | X | 78538296 | AAGCAggaGCAAAGTCACA TCTtACaTTGCGcgGCAT (SEQ ID NO: 87) | 8 | — |
| OT13 | 2 | 108000000 | ATGTAattcCAAAGTCCTCCA TGACcTgGCtTcTACCT (SEQ ID NO: 88) | 8 | — |
| OT14 | 8 | 28249779 | CTaCAaAttCAAtGaCAGTAG AGACTTTGCtTtTACTT (SEQ ID NO: 89) | 8 | — |
| OT15 | 9 | 93810846 | ATGCAacaGCAAgagCAGCA TGACTTTGttTtTcCTT (SEQ ID NO: 90) | 10 | — |
| TRAC | 14 | 23016627 | GTGCTGTgGCCTGGaGcAAC AAATCTGACTTTGCaTGTG CAA (SEQ ID NO: 91) | 4 | TRAC |

TABLE 14

Potential off target sites for TRBC-specific ZFNs

| Label | chromo-some | Start site | Sequence | # mismatches | Gene |
|---|---|---|---|---|---|
| C1 | 1 | 236659757 | CCcAagCCAGggCTACTGCTG GGTgGAACTGGACATGC (SEQ ID NO: 92) | 6 | — |

TABLE 14-continued

Potential off target sites for TRBC-specific ZFNs

| Label | chromo some | Start site | Sequence | # mismatches | Gene |
|---|---|---|---|---|---|
| C10 | 10 | 90573967 | CCcTGTgCgGTTCTgCTTAAC AGTAGAACaGGACActT (SEQ ID NO: 93) | 7 | LIPM |
| C5 | 5 | 165037707 | ACATGTCagaTTCTACATGA GGTAGAACTGttCTTGT (SEQ ID NO: 94) | 5 | — |
| C2 | 2 | 71186796 | ACAAGggCAGcTCTgtCCAAG GTAGcACTGGgCCTGT (SEQ ID NO: 95) | 7 | ATP6V1B1 |
| C15 | 15 | 75401377 | CgATGTCCAGaTgTACCTCA GGaAGgACTGGcCCTGG (SEQ ID NO: 96) | 6 | — |
| C3 | 3 | 159730398 | CCAAGTCCtccTCTAgGAAGG GGTAGAACTGGAaTTtG (SEQ ID NO: 97) | 6 | — |
| C1.2 | 1 | 60766812 | GaAGGTCCAGTgCaAtGTTGA aTAGAAgTGGACATcT (SEQ ID NO: 98) | 7 | — |
| C17 | 17 | 11136639 | AgAGGcCCAcTcCTAgAAGG GGTAGAcCTGGAtCTGG (SEQ ID NO: 99) | 7 | — |
| C15.2 | 15 | 67440002 | CCAGGTCCAGTTCTACCAG CCacAGAtgTGagCATGT (SEQ ID NO: 100) | 6 | SMAD3 |
| C2.2 | 2 | 120313989 | ACAAtTCCAGTTCaAgAATCT TtTAaAggTGGACATGG (SEQ ID NO: 101) | 7 | PCDP1 |
| C6 | 6 | 166419926 | GCtGGTgCAGcTCTACACGG ATGcAGAgCTGGtCCTcC (SEQ ID NO: 102) | 7 | — |
| C2.3 | 2 | 114733178 | CCtGGgCCAGTgCTgCTTGTC cTtGAACcGGgCCTGG (SEQ ID NO: 103) | 8 | — |
| C7.2 | 7 | 4224762 | GgAGaTCCAGTgCgACAGTC AGaAGAAggGGACTcGG (SEQ ID NO: 104) | 8 | SDK1 |
| CX | X | 73070675 | CTaCAaAttCAAtGaCAGTA GAGACTTTGCtTtTACTT (SEQ ID NO: 105) | 8 | XIST |
| CX.2 | X | 130414175 | CCAGGTCagGTTCcggAAAGA AGTAGAACTtGACCccT (SEQ ID NO: 106) | 8 | AGSF1 |
| TRBC | 7 | 142499011 | TCAAGTCCAGTTCTACGGGCT CtCGGAGaATGACGAGTGGA (SEQ ID NO: 107) | 2 | TRBC |

Figure 18:
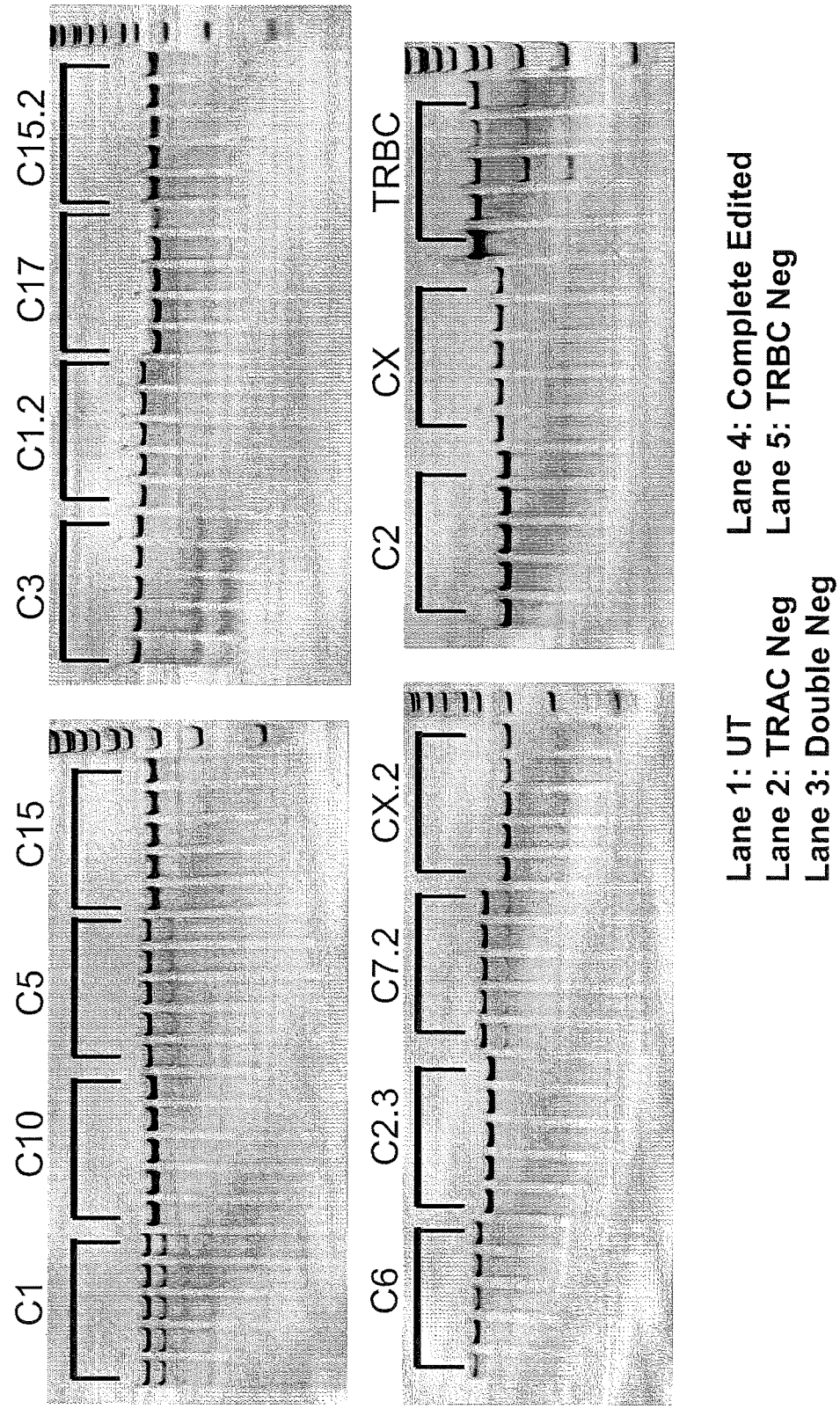
FIG. 18 depicts analysis for off-target cleavage by TRBC-specific ZFNs. 15 potential off target sites for the TRBC-specific ZNS (identified by in silicio analysis) were analyzed following ZFN treatment for cleavage by the Cel-I mismatch assay. Each potential off target site was analyzed in 5 samples: untransduced samples (UT), samples that were TRAC negative following TRAC-specific ZFN treatment and sorting (TRAC neg), cells that were TRAC and TRBC negative following sequential treatment with TRAC-specific ZFNs, the TRAC transgene and TRBC-specific ZFNs with sequential rounds of sorting (Double Neg), cells that were negative for the endogenous TRAC and TRBC loci following ZFN treatment as well as modified to comprise non-wild type TRAC and TRBC transgenes (Complete Edited), or TRBC negative following treatment with TRBC-specific ZFNs alone and sorting (TRBC Neg). Off target sites are as labeled in Table 14. TRBC depicts modification of the intended target site in these samples.

As can be seen from the data shown in FIGS. 17 and 18, there are no additional bands present in the off-site samples that have been treated with the ZFNs as compared to those that have not been transduced with the ZFN expression vectors (also compare with the TRAC and TRBC loci). Note that for technical issued relating to the PCR of the target, the C2.2 potential off target has not yet been fully analyzed. Nevertheless, it appears that the TRAC- and TRBC-specific ZFNs have a great deal of specificity for their intended targets.

What is claimed is:

1. An isolated genetically modified cell comprising a genomic modification that modifies the endogenous T-cell receptor (TCR) gene, wherein the genomic modification is selected from the group consisting of insertions, deletions and combinations thereof, wherein the genomic modification is produced by a zinc finger nuclease comprising a zinc finger protein that binds to a target site in the TCR gene, wherein said target site is any of SEQ ID NO: 1, 7, 13, 18, 23, 29, 34, 37, 41, 45, 49, 54, 58 or 63, wherein the binding of the zinc finger protein at the target site in the TCR gene results in cleavage of the TCR gene such that the TCR gene is modified within any of SEQ ID NO: 1, 7, 13, 18, 23, 29, 34, 37, 41, 45, 49, 54, 58 and 63, thereby resulting in a genetically modified cell comprising the genomic modification at the endogenous TCR gene.

2. The genetically modified cell of claim 1, wherein the genomic modification is within an endogenous TCRα or TCRβ gene.

3. The genetically modified cell of claim 2, wherein the genomic modification is within exon 1 or exon 3 of an endogenous TCRα gene.

4. The genetically modified cell of claim 1, wherein the endogenous TCR gene is inactivated.

5. The genetically modified cell of claim 1, wherein the cell is a T-cell.

6. The genetically modified cell of claim 1, wherein the cell is a stem cell.

7. The genetically modified cell of claim 6, wherein the stem cell is a hematopoietic stem cell.

8. A genetically modified differentiated cell descended from the stem cell of claim 6.

9. The isolated genetically modified cell of claim 1, wherein the zinc finger nuclease is introduced into the cell as a polynucleotide.

10. The genetically modified cell of claim 1, further comprising a donor polynucleotide encoding a transgene.

11. The genetically modified cell of claim 10, wherein the transgene encodes an engineered T cell receptor subunit.

12. The genetically modified cell of claim 10, wherein the transgene encodes a chimeric antigen receptor (CAR).

13. A pharmaceutical composition comprising the genetically modified cell of claim 1.

* * * * *